(12) United States Patent
Justino et al.

(10) Patent No.: US 11,464,632 B2
(45) Date of Patent: Oct. 11, 2022

(54) TRANSCATHETER AND SERIALLY-EXPANDABLE ARTIFICIAL HEART VALVE

(71) Applicants: Baylor College of Medicine, Houston, TX (US); William Marsh Rice University, Houston, TX (US)

(72) Inventors: Henri Justino, Houston, TX (US); Daniel Harrington, Houston, TX (US); Kwonsoo Chun, Katy, TX (US)

(73) Assignees: Baylor College of Medicine, Houston, TX (US); William Marsh Rice University, Houston, TX (US)

( * ) Notice: Subject to any disclaimer, the term of this patent is extended or adjusted under 35 U.S.C. 154(b) by 0 days.

(21) Appl. No.: 17/473,653

(22) Filed: Sep. 13, 2021

(65) Prior Publication Data

US 2022/0117731 A1    Apr. 21, 2022

Related U.S. Application Data

(63) Continuation of application No. 16/563,229, filed on Sep. 6, 2019, which is a continuation of application
(Continued)

(51) Int. Cl.
*A61F 2/24* (2006.01)
*A61F 2/91* (2013.01)
(Continued)

(52) U.S. Cl.
CPC .......... *A61F 2/2433* (2013.01); *A61F 2/2418* (2013.01); *A61F 2/2415* (2013.01);
(Continued)

(58) Field of Classification Search
CPC ........ A61F 2/2415; A61F 2/2418; A61F 2/91; A61F 2250/001; A61F 2250/0082
See application file for complete search history.

(56) References Cited

U.S. PATENT DOCUMENTS

| 3,655,306 A | 4/1972 | Ross et al. |
| 3,657,744 A | 4/1972 | Ersek |

(Continued)

FOREIGN PATENT DOCUMENTS

| DE | 19546692 C2 | 11/2002 |
| EP | 1395205 B1 | 7/2008 |

(Continued)

OTHER PUBLICATIONS

Bavaria, J. E. et al., "The St Jude Medical Trifecta aortic pericardial valve: Results from a global, multicenter, prospective clinical study," The Journal of Thoracic and Cardiovascular Surgery, 147(2):590-597 (Feb. 2014).

(Continued)

*Primary Examiner* — Suba Ganesan

(57) ABSTRACT

Some embodiments are directed to a transcatheter and serially-expandable artificial heart valve, e.g., to be minimally-invasively implanted into a pediatric patient during a first procedure, and then expanded during a second procedure to accommodate for the pediatric patient's growth. Some embodiments include an expandable frame having a compressed, delivery configuration, and an expanded, deployed configuration, in which the valve is implantable within the patient. The valve can have a first working condition when the frame is expanded to a first diameter and a second working condition when the frame is expanded to a second diameter greater than the first diameter. The valve can include a plurality of leaflets configured to accommodate the expansion of the frame and growth of the patient.

23 Claims, 30 Drawing Sheets

Related U.S. Application Data

No. 15/308,667, filed as application No. PCT/US2015/029442 on May 6, 2015, now abandoned.

(60) Provisional application No. 61/989,820, filed on May 7, 2014.

(51) Int. Cl.
*A61L 27/34* (2006.01)
*A61L 27/50* (2006.01)

(52) U.S. Cl.
CPC ......... *A61F 2/91* (2013.01); *A61F 2210/0076* (2013.01); *A61F 2220/005* (2013.01); *A61F 2220/0008* (2013.01); *A61F 2220/0058* (2013.01); *A61F 2230/005* (2013.01); *A61F 2230/0008* (2013.01); *A61F 2230/0019* (2013.01); *A61F 2230/0069* (2013.01); *A61F 2250/001* (2013.01); *A61F 2250/0029* (2013.01); *A61F 2250/0036* (2013.01); *A61F 2250/0037* (2013.01); *A61F 2250/0082* (2013.01); *A61F 2250/0098* (2013.01); *A61L 27/34* (2013.01); *A61L 27/507* (2013.01)

(56) References Cited

U.S. PATENT DOCUMENTS

| | | | |
|---|---|---|---|
| 3,744,060 A | 7/1973 | Bellhouse et al. |
| 4,056,854 A | 11/1977 | Boretos et al. |
| 4,731,074 A | 3/1988 | Rousseau et al. |
| 4,778,461 A | 10/1988 | Pietsch et al. |
| 5,326,371 A | 7/1994 | Love et al. |
| 5,411,552 A | 5/1995 | Andersen et al. |
| 5,500,016 A | 3/1996 | Fisher |
| 5,509,930 A | 4/1996 | Love |
| 5,562,729 A | 10/1996 | Purdy et al. |
| 5,674,279 A | 10/1997 | Wright et al. |
| 5,840,081 A | 11/1998 | Andersen et al. |
| 5,855,597 A | 1/1999 | Jayaraman |
| 5,855,601 A | 1/1999 | Bessler et al. |
| 5,957,949 A | 9/1999 | Leonhardt et al. |
| 6,086,612 A | 7/2000 | Jansen |
| 6,092,529 A | 7/2000 | Cox |
| 6,113,631 A | 9/2000 | Jansen |
| 6,117,169 A | 9/2000 | Moe |
| 6,168,614 B1 | 1/2001 | Andersen et al. |
| 6,171,335 B1 | 1/2001 | Wheatley et al. |
| 6,206,911 B1 | 3/2001 | Milo |
| 6,270,526 B1 | 8/2001 | Cox |
| 6,299,637 B1 | 10/2001 | Shaolian et al. |
| 6,454,798 B1 | 9/2002 | Moe |
| 6,458,153 B1 | 10/2002 | Bailey et al. |
| 6,482,228 B1 | 11/2002 | Norred |
| 6,562,069 B2 | 5/2003 | Cai et al. |
| 6,582,462 B1 | 6/2003 | Andersen et al. |
| 6,596,024 B2 | 7/2003 | Chinn |
| 6,652,578 B2 | 11/2003 | Bailey et al. |
| 6,716,241 B2 | 4/2004 | Wilder et al. |
| 6,736,845 B2 | 5/2004 | Marquez et al. |
| 6,911,043 B2 | 6/2005 | Myers et al. |
| 6,916,338 B2 | 7/2005 | Speziali |
| 6,953,332 B1 | 10/2005 | Kurk et al. |
| 6,958,076 B2 | 10/2005 | Acosta et al. |
| 7,018,408 B2 | 3/2006 | Bailey et al. |
| 7,041,132 B2 | 5/2006 | Quijano et al. |
| 7,101,396 B2 | 9/2006 | Artof et al. |
| 7,125,418 B2 | 10/2006 | Duran et al. |
| 7,160,320 B2 | 1/2007 | Duran |
| 7,195,641 B2 | 3/2007 | Palmaz et al. |
| 7,261,732 B2 | 8/2007 | Justino |
| 7,329,279 B2 | 2/2008 | Haug et al. |
| 7,338,520 B2 | 3/2008 | Bailey et al. |
| 7,510,572 B2 | 3/2009 | Gabbay |
| 7,510,575 B2 | 3/2009 | Spenser et al. |
| 7,534,259 B2 | 5/2009 | Lashinski et al. |
| 7,547,322 B2 | 6/2009 | Sarac et al. |
| 7,556,645 B2 | 7/2009 | Lashinski et al. |
| 7,569,071 B2 | 8/2009 | Haverkost et al. |
| 7,604,661 B2 | 10/2009 | Pavcnik et al. |
| 7,618,446 B2 | 11/2009 | Andersen et al. |
| 7,628,803 B2 | 12/2009 | Pavcnik et al. |
| 7,648,527 B2 | 1/2010 | Agnew |
| 7,682,389 B2 | 3/2010 | Beith |
| 7,799,069 B2 | 9/2010 | Bailey et al. |
| 7,803,185 B2 | 9/2010 | Gabbay |
| 7,806,920 B2 | 10/2010 | Duran |
| 7,833,565 B2 | 11/2010 | O'Connor et al. |
| 8,109,996 B2 | 2/2012 | Stacchino et al. |
| 8,216,631 B2 | 7/2012 | O'Connor et al. |
| 8,246,678 B2 | 8/2012 | Salahieh et al. |
| 8,512,397 B2 | 8/2013 | Rolando et al. |
| 8,535,373 B2 | 9/2013 | Stacchino et al. |
| 8,540,768 B2 | 9/2013 | Stacchino et al. |
| 8,613,763 B2 | 12/2013 | Pavcnik et al. |
| 9,259,313 B2 | 2/2016 | Wheatley |
| 9,421,100 B2 | 8/2016 | Bailey et al. |
| 9,603,707 B2 | 3/2017 | Li |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2002/0032481 A1 | 3/2002 | Gabbay |
| 2002/0151971 A1 | 10/2002 | Cox |
| 2003/0036795 A1 | 2/2003 | Andersen et al. |
| 2003/0040792 A1 | 2/2003 | Gabbay |
| 2003/0097175 A1* | 5/2003 | O'Connor ............ A61F 2/2412 623/910 |
| 2003/0109924 A1 | 6/2003 | Cribier |
| 2003/0114924 A1 | 6/2003 | Moe |
| 2004/0088045 A1 | 5/2004 | Cox |
| 2004/0088046 A1 | 5/2004 | Speziali |
| 2004/0106976 A1 | 6/2004 | Bailey et al. |
| 2004/0210304 A1 | 10/2004 | Seguin et al. |
| 2004/0215333 A1 | 10/2004 | Duran et al. |
| 2005/0055079 A1 | 3/2005 | Duran |
| 2005/0137676 A1 | 6/2005 | Richardson et al. |
| 2005/0137681 A1 | 6/2005 | Shoemaker et al. |
| 2005/0209689 A1 | 9/2005 | Speziali |
| 2005/0267560 A1 | 12/2005 | Bates |
| 2005/0283231 A1 | 12/2005 | Haug et al. |
| 2006/0020333 A1 | 1/2006 | Lashinski et al. |
| 2006/0020334 A1 | 1/2006 | Lashinski et al. |
| 2006/0052867 A1 | 3/2006 | Revuelta et al. |
| 2006/0089708 A1 | 4/2006 | Osse et al. |
| 2006/0122693 A1 | 6/2006 | Biadillah et al. |
| 2006/0200234 A1 | 9/2006 | Hines |
| 2006/0206192 A1 | 9/2006 | Tower et al. |
| 2006/0241744 A1 | 10/2006 | Beith |
| 2006/0282157 A1 | 12/2006 | Hill et al. |
| 2007/0010877 A1 | 1/2007 | Salahieh et al. |
| 2007/0027535 A1 | 2/2007 | Purdy, Jr. et al. |
| 2007/0050013 A1 | 3/2007 | Gross |
| 2007/0050014 A1 | 3/2007 | Johnson |
| 2007/0050021 A1 | 3/2007 | Johnson |
| 2007/0061009 A1 | 3/2007 | Spenser et al. |
| 2007/0078510 A1 | 4/2007 | Ryan |
| 2007/0129788 A1 | 6/2007 | Drasler et al. |
| 2007/0208550 A1 | 9/2007 | Cao et al. |
| 2007/0213813 A1 | 9/2007 | Von Segesser et al. |
| 2007/0282436 A1 | 12/2007 | Pinchuk |
| 2007/0288087 A1 | 12/2007 | Fearnot et al. |
| 2008/0086204 A1 | 4/2008 | Rankin |
| 2008/0091261 A1 | 4/2008 | Long et al. |
| 2008/0161911 A1 | 7/2008 | Revuelta et al. |
| 2008/0200980 A1 | 8/2008 | Robin et al. |
| 2009/0062907 A1 | 3/2009 | Quijano et al. |
| 2009/0138079 A1 | 5/2009 | Tuval et al. |
| 2009/0171456 A1 | 7/2009 | Kveen et al. |
| 2009/0222085 A1 | 9/2009 | Kumar |
| 2009/0248149 A1 | 10/2009 | Gabbay |
| 2009/0254177 A1 | 10/2009 | Yang et al. |
| 2009/0281609 A1 | 11/2009 | Benichou et al. |
| 2009/0281619 A1 | 11/2009 | Le et al. |

(56) References Cited

U.S. PATENT DOCUMENTS

| | | |
|---|---|---|
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2010/0004740 A1 | 1/2010 | Seguin et al. |
| 2010/0005658 A1 | 1/2010 | Haverkost et al. |
| 2010/0018447 A1 | 1/2010 | Holecek et al. |
| 2010/0055149 A1 | 3/2010 | Li et al. |
| 2010/0057191 A1 | 3/2010 | Pavcnik et al. |
| 2010/0057194 A1 | 3/2010 | Ryan |
| 2010/0076548 A1 | 3/2010 | Konno |
| 2010/0094411 A1 | 4/2010 | Tuval et al. |
| 2010/0114307 A1 | 5/2010 | Agnew et al. |
| 2010/0131055 A1 | 5/2010 | Case et al. |
| 2010/0145435 A1 | 6/2010 | Voinov et al. |
| 2010/0152839 A1 | 6/2010 | Shandas et al. |
| 2010/0168832 A1 | 7/2010 | Neuenschwander |
| 2010/0174362 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0249894 A1 | 9/2010 | Oba et al. |
| 2010/0286769 A1 | 11/2010 | Andersen et al. |
| 2010/0305685 A1 | 12/2010 | Millwee et al. |
| 2011/0257738 A1 | 10/2011 | Corbett et al. |
| 2011/0257739 A1* | 10/2011 | Corbett ................. A61F 2/2412 623/2.18 |
| 2012/0053676 A1 | 3/2012 | Ku et al. |
| 2012/0078347 A1 | 3/2012 | Braido et al. |
| 2012/0123529 A1 | 5/2012 | Levi et al. |
| 2012/0179244 A1 | 7/2012 | Schankereli et al. |
| 2012/0197390 A1* | 8/2012 | Alkhatib ............... A61F 2/2418 623/2.18 |
| 2012/0277856 A1 | 11/2012 | Spenser et al. |
| 2013/0073037 A1 | 3/2013 | Gregg et al. |
| 2013/0085566 A1 | 4/2013 | Forster et al. |
| 2013/0160512 A1 | 6/2013 | Chen |
| 2013/0325116 A1 | 12/2013 | Sundler et al. |
| 2014/0005772 A1 | 1/2014 | Edelman et al. |
| 2014/0005773 A1 | 1/2014 | Wheatley |
| 2014/0031927 A1 | 1/2014 | Bruchman et al. |
| 2014/0107772 A1 | 4/2014 | Li et al. |
| 2014/0316516 A1 | 10/2014 | Vidlund et al. |
| 2014/0330367 A1 | 11/2014 | Thapliyal |
| 2015/0088250 A1 | 3/2015 | Zeng et al. |
| 2016/0067038 A1* | 3/2016 | Park ...................... A61F 2/2415 623/2.18 |
| 2016/0158000 A1 | 6/2016 | Granada et al. |
| 2017/0014228 A1 | 1/2017 | Emani et al. |
| 2017/0086971 A1 | 3/2017 | Braido et al. |
| 2017/0189172 A1 | 7/2017 | Grundeman et al. |
| 2017/0189175 A1* | 7/2017 | Justino .................. A61F 2/2415 |
| 2019/0117391 A1* | 4/2019 | Humair ................. A61F 2/2418 |
| 2019/0133764 A1* | 5/2019 | Carr ...................... A61F 2/2412 |
| 2019/0282360 A1* | 9/2019 | Colavito ............... A61F 2/2418 |
| 2019/0374339 A1 | 12/2019 | Bennett |
| 2019/0388221 A1* | 12/2019 | Lee ....................... A61F 2/2436 |
| 2020/0000581 A1 | 1/2020 | Justing et al. |
| 2021/0137676 A1* | 5/2021 | Kheradvar ............ A61F 2/2415 |

FOREIGN PATENT DOCUMENTS

| | | |
|---|---|---|
| WO | WO-0141679 A1 | 6/2001 |
| WO | WO-021 00301 A1 | 12/2002 |
| WO | WO-2012110767 A2 | 8/2012 |
| WO | WO-2013019416 A1 | 2/2013 |
| WO | WO-2014209232 A1 | 12/2014 |
| WO | WO-2015171743 A2 | 11/2015 |

OTHER PUBLICATIONS

Claiborne, T. E. et al., "Polymeric trileaflet prosthetic heart valves: evolution and path to clinical reality," Expert Rev. Med. Devices, 9(6):577-594 (Nov. 2012).

Cribier, A. et al., "Early Experience With Percutaneous Transcatheter Implantation of Heart Valve Prosthesis for the Treatment of End-Stage Inoperable Patients With Calcific Aortic Stenosis," Journal of the American College of Cardiology, 43(4):698-703 (2004).

De Tullio, M. D., et al., "Direct numerical simulation of the pulsatile flow through an aortic bileaflet mechanical heart valve," J. Fluid Meeh., 622:259-290 (Mar. 2009).

Extended European Search Report for European Patent Application No. 15789240.7, dated Feb. 23, 2018, 9 pages.

International Search Report and Written Opinion for International Patent Application No. PCT/US2015/029442, dated Nov. 9, 2015, 13 pages.

Jiang, H. et al., "Design and manufacture of a polyvinyl alcohol (PVA) cryogel tri-leaflet heart valve prosthesis," Medical Engineering & Physics, vol. 26, pp. 269-277, 2004.

Leat, M. E., et al., "A synthetic leaflet heart valve with improved opening characteristics," Med. Eng. Phys., 16:170-476 (Nov. 1994).

Leat, M. E. et al., "The influence of manufacturing methods on the function and performance of a synthetic leaflet heart valve," Proc Instn Meeh Engrs, 209:65-69 (1995).

Leo, H. L., "An In Vitro Investigation of the Flow Fields Through Bileaflet and Polymeric Prosthetic Heart Valves," A Dissertation Presented to the Academic Faculty In Partial Fulfillment of the Requirements for the Degree of Doctor of Philosophy in Biomedical Engineering, Georgia Institute of Technology, Apr. 2005.

Mackay, T. G. et al., "New polyurethane heart valve prosthesis: design, manufacture and evaluation," Biomaterials, 17:1857-1863 (1996).

MedGadget, "Sorin Mitroflow Aortic Heart Valve With New Phospholipid Reduction Treatment Approved by FDA," [Online], http://medgadget.com/2014/04/sorin-mitroflow-aortic-heart-valve-with-new-phospholipid-reduction-treatment-approved-by-fda.html, Retrieved on May 2014.

Metzner, A. et al., "Percutaneous pulmonary polyurethane valved stent implantation," The Journal of Thoracic and Cardiovascular Surgery, 139(3):748-752 (Mar. 2010).

Office Action for U.S. Appl. No. 15/308,667, dated Feb. 14, 2018, 14 pages.

Office Action for U.S. Appl. No. 15/308,667, dated Oct. 9, 2018, 16 pages.

Office Action for U.S. Appl. No. 16/563,229, dated Apr. 7, 2020, 28 pages.

Office Action for U.S. Appl. No. 16/563,229, dated Dec. 20, 2019, 22 pages.

Office Action for U.S. Appl. No. 16/563,229, dated Feb. 22, 2021, 25 pages.

Permanyer, E. et al., "St. Jude Medical Trifecta™ aortic valve perioperative performance in 200 patients," Interactive Cardiovascular and Thoracic Surgery, 17:669-673 (2013).

Sanders, E. H. et al., "Composite Finite Element Model of a Stented Bioprosthetic Heart Valve," 291-302, Apr. 7, 2015.

U.S. Food and Drug Administration, St. Jude Medical Trifecta Valve—P100029, [Online], http://www.fda.gov/MedicalDevices/ProductsandMedicalProcedures/De . . . , Retrieved May 2016.

Valocik, G. et al., "Three-Dimensional Echocardiography in Mitral Valve Disease," Eur J Echocardiogr, 6:443-454 (2005).

Webb, J. G. et al., "Transcatheter Aortic Valve Replacement for Bioprosthetic Aortic Valve Failure The Valve-in-Valve Procedure," Circulation, 127:2542-2550 (Jun. 2013).

Zilla, P. et al., "Prosthetic heart valves: Catering for the few," Biomaterials, 29:385-406 (2008).

Office Action for U.S. Appl. No. 17/478,665, dated Jan. 21, 2022, 17 pages.

Office Action for Canadian Application No. 2,948,179, dated Mar. 1, 2022, 5 pages.

* cited by examiner

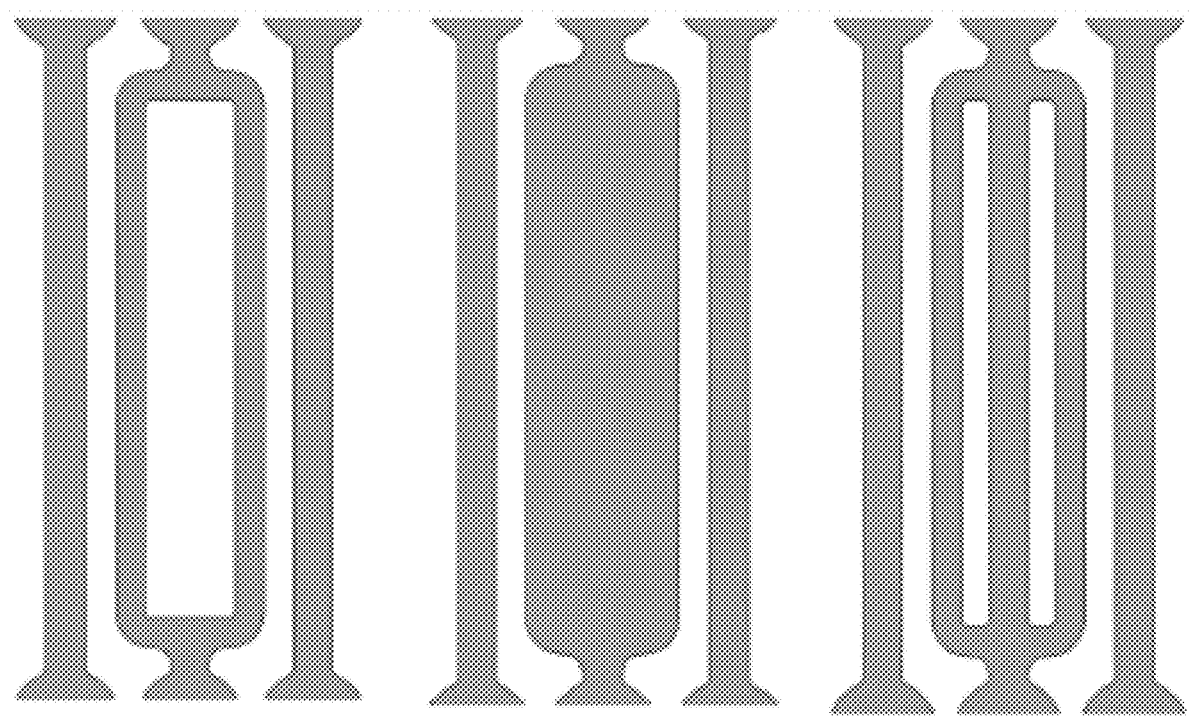
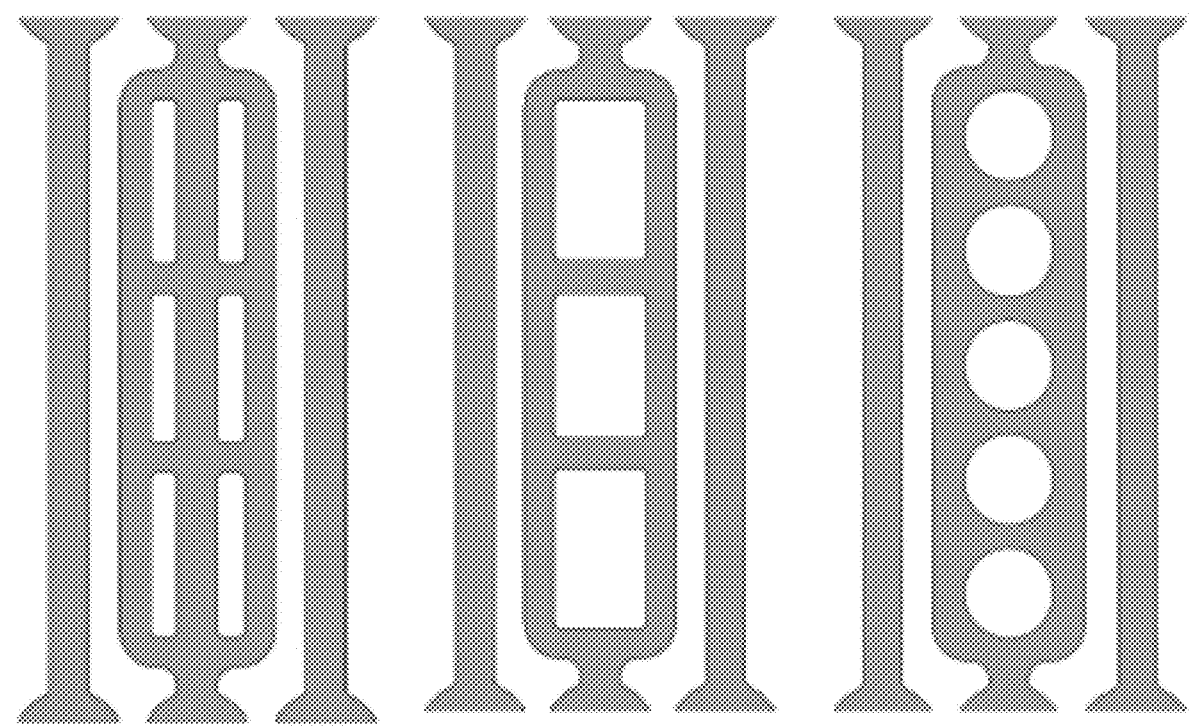
FIG. 4

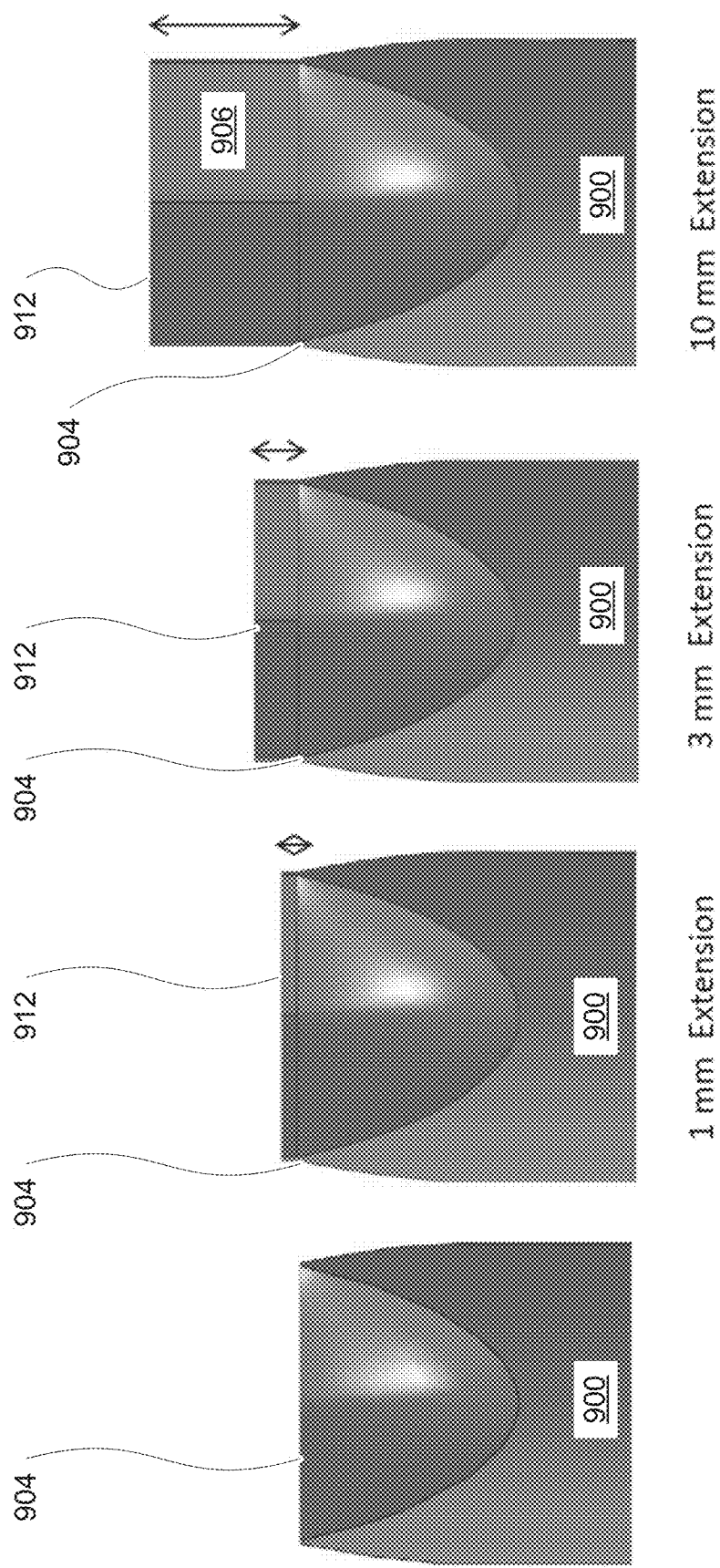

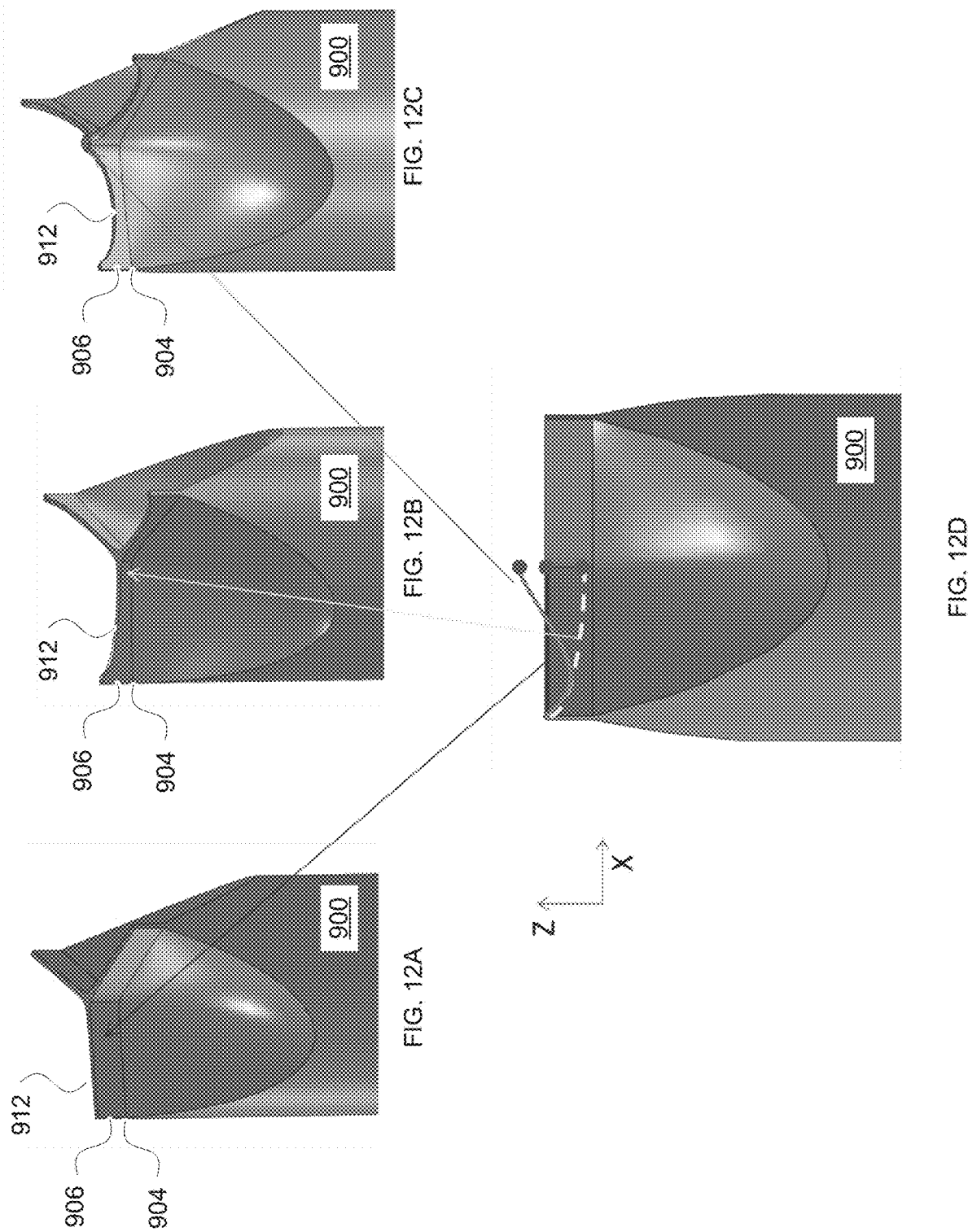

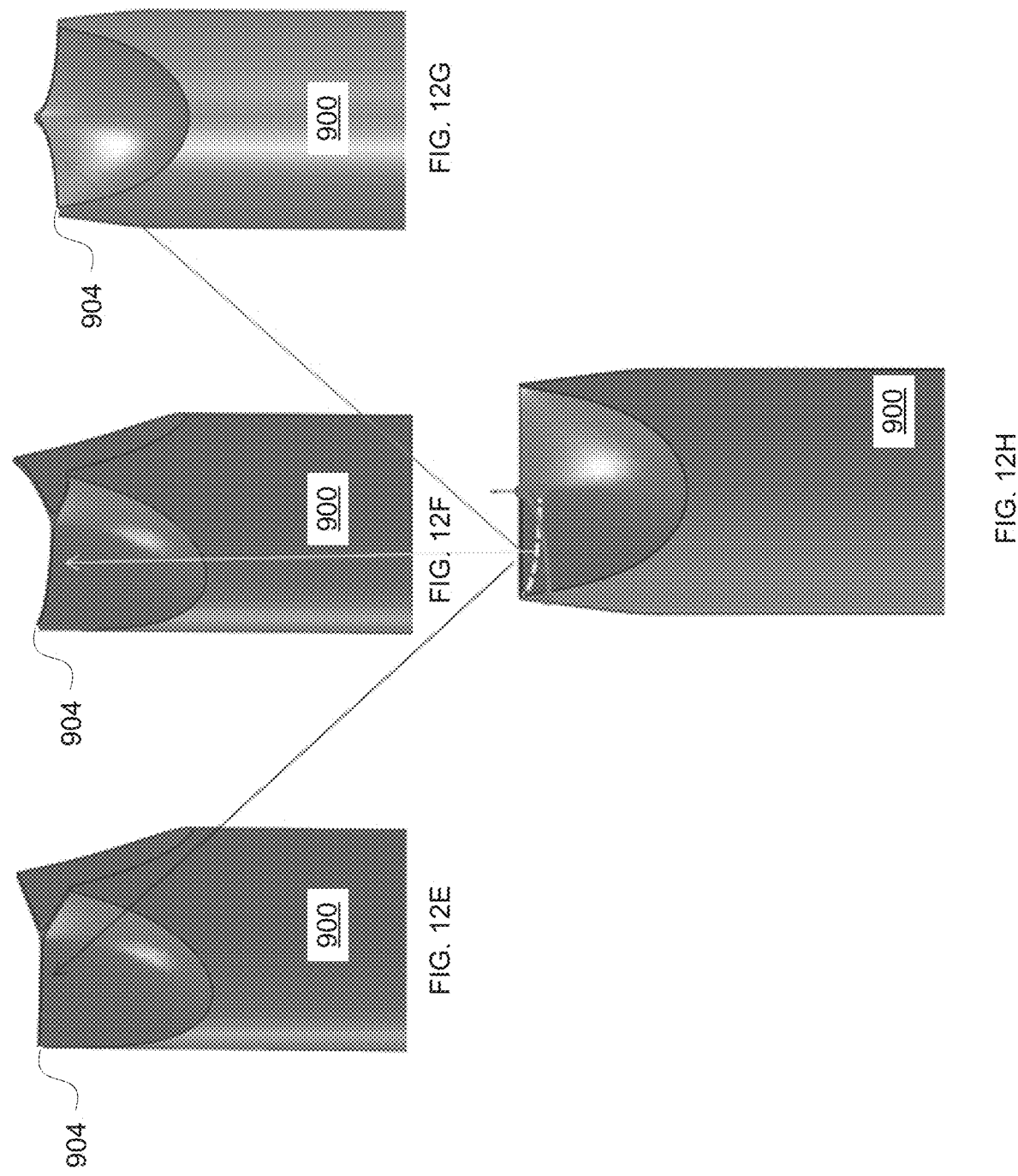

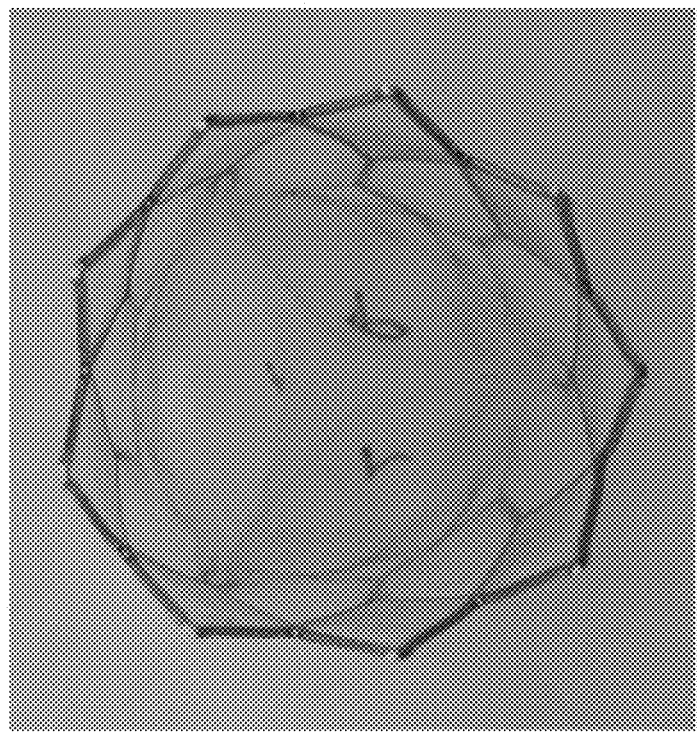
FIG. 17A
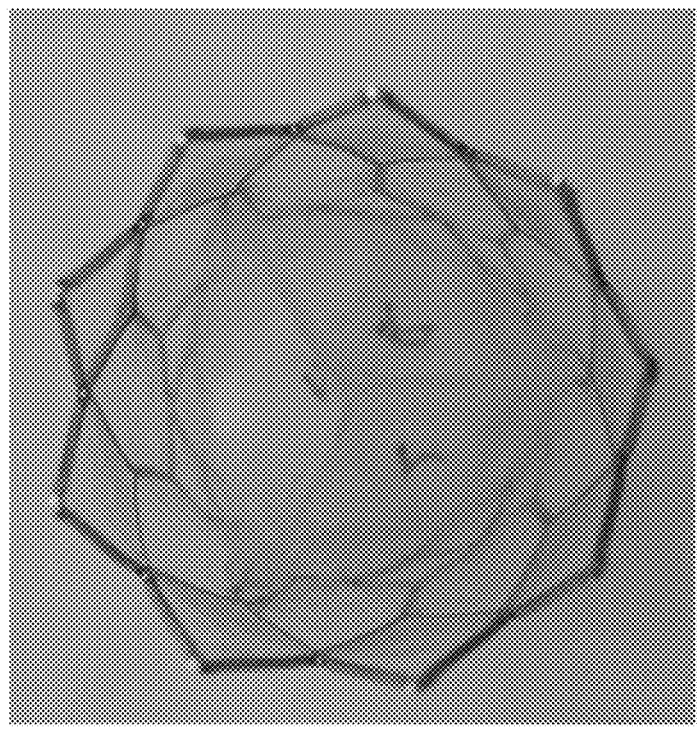
FIG. 17B

TRANSCATHETER AND SERIALLY-EXPANDABLE ARTIFICIAL HEART VALVE

CROSS-REFERENCE TO RELATED APPLICATIONS

This application is a continuation of U.S. patent application Ser. No. 16/563,229, filed Sep. 6, 2019, which is a continuation of U.S. patent application Ser. No. 15/308,667, filed Nov. 3, 2016, which is a 371 national stage entry of International Application No. PCT/US2015/029442, filed May 6, 2015, which claims priority to U.S. Provisional Patent Application Ser. No. 61/989,820, filed May 7, 2014. The entire content of these applications is hereby incorporated by reference herein.

BACKGROUND OF THE INVENTION

Valves exist in the body (e.g., in the heart and the systemic veins) to allow unidirectional blood flow. A variety of congenital conditions, infectious diseases (e.g., endocarditis), rheumatic heart disease, and age-related impairments (e.g., senile stenosis) can necessitate implantation of an artificial valve.

SUMMARY OF THE INVENTION

One aspect of the invention provides an artificial, flexible valve including: a stent defining a wall and a plurality of leaflets extending from the wall of the stent. The plurality of leaflets form a plurality of coaptation regions between two adjacent leaflets. The coaptation regions include extensions along a z-axis and adapted and are configured to form a releasable, but substantially complete seal when the leaflets are in a closed position.

This aspect of the invention can have a variety of embodiments. The extensions can have a length along the z-axis between about 1 mm and about 10 mm. The extensions can have a curved profile. The curved profile can lie in an x-y plane. The curved profile can be a variance in extension length along the z-axis.

The coaptation regions can have a substantially hyperbolic profile. Each of the plurality of leaflets can have a substantially elliptical leaflet-stent attachment line. The stent can be an expandable, cylindrical stent. The leaflets can be reinforced with one or more selected from the group consisting of: reinforcing materials and directional fibers. One or more selected from the group consisting of: coaptation regions and leaflet-stent attachment lines can be reinforced with one or more selected from the group consisting of: additional polymer thickness, reinforcing materials, and directional fibers.

Adjacent leaflets can be coupled to a wide post of the stent. The wide post can include one or more windows. The wide post can have a width between about 0.5 mm and about 3 mm.

The stent can include metal or plastic. The metal can be selected from the group consisting of: stainless steel, 316L stainless steel, cobalt-chromium alloys, and nickel-titanium alloys.

The leaflets can be formed from a first polymer. The first polymer can be selected from the group consisting of: polytetrafluoroethylene, polyethylene, polyurethane, silicone, and copolymers thereof.

The stent can be dip-coated in a second polymer. The second polymer can be selected from the group consisting of: polytetrafluoroethylene, polyethylene, polyurethane, silicone, and copolymers thereof. The leaflets can be coupled to the second polymer. The leaflets can be mechanically coupled to the second polymer. The leaflets can be chemically coupled to the second polymer. The leaflets can be coupled to the second polymer by one or more techniques selected from the group consisting of: gluing, chemical fusing, thermal fusing, sonic welding, stitching, and mechanical fastening.

A leaflet-stent attachment line for each of the plurality of leaflets can substantially approximate a frame of the stent. The leaflet-stent attachment line can lie within about 3 mm of the frame of the stent.

The stent can include one or more anchor points. The anchor points can contain a radio-opaque material.

The valve can be adapted and configured for replacement of one or more cardiac valves selected from the group consisting of: aortic, mitral, tricuspid, and pulmonary.

The valve can be adapted and configured for insertion in a subject's veins in order to treat venous insufficiency. The valve can be adapted and configured for serial expansion as the subject ages.

Another aspect of the invention provides an artificial, flexible valve including: a stent defining a wall and a plurality of leaflets extending from the wall of the stent. Each of the plurality of leaflets terminates in a commissure line. The commissure lines deviate from a hyperbola formed in the x-y plane by at least one deviation selected from the group consisting of: a deviation in the z-direction and one or more curves relative to the hyperbola.

This aspect of the invention can have a variety of embodiments. The leaflets can further include extensions beyond the commissure lines along a z-axis. The extensions can have a length along the z-axis between about 1 mm and about 10 mm. The extensions can have a curved profile. The curved profile can lie in an x-y plane. The curved profile can be a variance in extension length along the z-axis.

Each of the plurality of leaflets can have a substantially elliptical leaflet-stent attachment line. The stent can have an expandable, cylindrical stent. The leaflets can be reinforced with one or more selected from the group consisting of: reinforcing materials and directional fibers.

One or more selected from the group consisting of: coaptation regions and leaflet-stent attachment lines can be reinforced with one or more selected from the group consisting of: additional polymer thickness, reinforcing materials, and directional fibers.

Adjacent leaflets can be coupled to a wide post of the stent. The wide post can include one or more windows. The wide post can have a width between about 0.5 mm and about 3 mm.

The stent can include metal or plastic. The metal can be selected from the group consisting of: stainless steel, 316L stainless steel, cobalt-chromium alloys, and nickel-titanium alloys.

The leaflets can be formed from a first polymer. The first polymer can be selected from the group consisting of: polytetrafluoroethylene, polyethylene, polyurethane, silicone, and copolymers thereof.

The stent can be dip-coated in a second polymer. The second polymer can be selected from the group consisting of: polytetrafluoroethylene, polyethylene, polyurethane, silicone, and copolymers thereof. The leaflets can be coupled to the second polymer. The leaflets can be mechanically coupled to the second polymer. The leaflets can be chemically coupled to the second polymer. The leaflets can be coupled to the second polymer by one or more techniques selected from the group consisting of: gluing, chemical fusing, thermal fusing, sonic welding, stitching, and mechanical fastening.

A leaflet-stent attachment line for each of the plurality of leaflets can substantially approximate a frame of the stent. The leaflet-stent attachment line can lie within about 3 mm of the frame of the stent.

The stent can include one or more anchor points. The anchor points can contain a radio-opaque material.

The valve can be adapted and configured for replacement of one or more cardiac valves selected from the group consisting of: aortic, mitral, tricuspid, and pulmonary.

The valve can be adapted and configured for insertion in a subject's veins in order to treat venous insufficiency. The valve can be adapted and configured for serial expansion as the subject ages.

Another aspect of the invention provides an artificial, flexible valve including: an expandable, cylindrical stent defining a wall and a plurality of leaflets extending from the wall of the stent. Adjacent leaflets can be coupled to a relatively wide post of the stent.

The leaflets can further include extensions beyond the commissure lines along a z-axis. The extensions can have a length along the z-axis between about 1 mm and about 10 mm. The extensions can have a curved profile. The curved profile can lie in an x-y plane. The curved profile can be a variance in extension length along the z-axis.

The coaptation regions can have a substantially hyperbolic profile. Each of the plurality of leaflets can have a substantially elliptical leaflet-stent attachment line. The leaflets can be reinforced with one or more selected from the group consisting of: reinforcing materials and directional fibers.

One or more selected from the group consisting of: coaptation regions and leaflet-stent attachment lines can be reinforced with one or more selected from the group consisting of: additional polymer thickness, reinforcing materials, and directional fibers.

The relatively wide post can include one or more windows. The relatively wide post can have a width between about 0.5 mm and about 3 mm.

The stent can include metal or plastic. The metal can be selected from the group consisting of: stainless steel, 316L stainless steel, cobalt-chromium alloys, and nickel-titanium alloys.

The leaflets can be formed from a first polymer. The first polymer can be selected from the group consisting of: polytetrafluoroethylene, polyethylene, polyurethane, silicone, and copolymers thereof.

The stent can be dip-coated in a second polymer. The second polymer can be selected from the group consisting of: polytetrafluoroethylene, polyethylene, polyurethane, silicone, and copolymers thereof. The leaflets can be coupled to the second polymer. The leaflets can be mechanically coupled to the second polymer. The leaflets can be chemically coupled to the second polymer. The leaflets can be coupled to the second polymer by one or more techniques selected from the group consisting of: gluing, chemical fusing, thermal fusing, sonic welding, stitching, and mechanical fastening.

A leaflet-stent attachment line for each of the plurality of leaflets can substantially approximate a frame of the stent. The leaflet-stent attachment line can lie within about 3 mm of the frame of the stent.

The stent can include one or more anchor points. The anchor points can contain a radio-opaque material.

The valve can be adapted and configured for replacement of one or more cardiac valves selected from the group consisting of: aortic, mitral, tricuspid, and pulmonary. The valve can be adapted and configured for insertion in a subject's veins in order to treat venous insufficiency. The valve can be adapted and configured for serial expansion as the subject ages. The valve may not contain any animal-derived materials.

Another aspect of the invention provides a mandrel including: a cylindrical profile and a plurality of recesses adapted and configured to define a plurality of leaflets forming a plurality of coaptation regions between two adjacent leaflets. The coaptation regions can include extensions along a z-axis and be adapted and configured to form a releasable, but substantially complete seal when the leaflets are in a closed position.

This aspect of the invention can have a variety of embodiments. The mandrel can include one more cutting guides located between the plurality of recesses. The mandrel can include one or more heating elements.

Another aspect of the invention provides a mandrel including: a cylindrical profile and a plurality of recesses adapted and configured to define a plurality of leaflets. Each of the plurality of leaflets terminate in a commissure line. The commissure lines deviate from a hyperbola formed in the x-y plane by at least one deviation selected from the group consisting of: a deviation in the z-direction and one or more curves relative to the hyperbola.

This aspect of the invention can have a variety of embodiments. The mandrel can include one more cutting guides located between the plurality of recesses. The mandrel can include one or more heating elements.

Another aspect of the invention provides a method for fabricating an artificial, flexible valve. The method includes: dip coating a cylindrical mandrel having a plurality of recesses each approximating a profile of a leaflet and coupling the leaflets to an inner wall of a stent.

This aspect of the invention can have a variety of embodiments. The method can further include dip coating the stent prior to coupling the leaflets to the inner wall of the stent. The stent and the mandrel can have larger diameters than a target location for the valve. The method can further include separating adjacent leaflets from each other.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein:

FIG. 4 depicts various vertical post geometries according to embodiments of the invention;

FIGS. 11A-11D depict mandrels for forming coaptation regions of varying height according to embodiments of the invention;

FIGS. 12A-12D depict mandrels for forming coaptation regions of varying radial length according to embodiments of the invention;

FIGS. 12E-12H depict mandrels for forming commissure lines having variable depths along the z-axis according to embodiments of the invention;

FIGS. 17A and 17B depict the compression of a valve after assembly in order to bring leaflets into contact with each other according to embodiments of the invention;

DEFINITIONS

Figure 1:
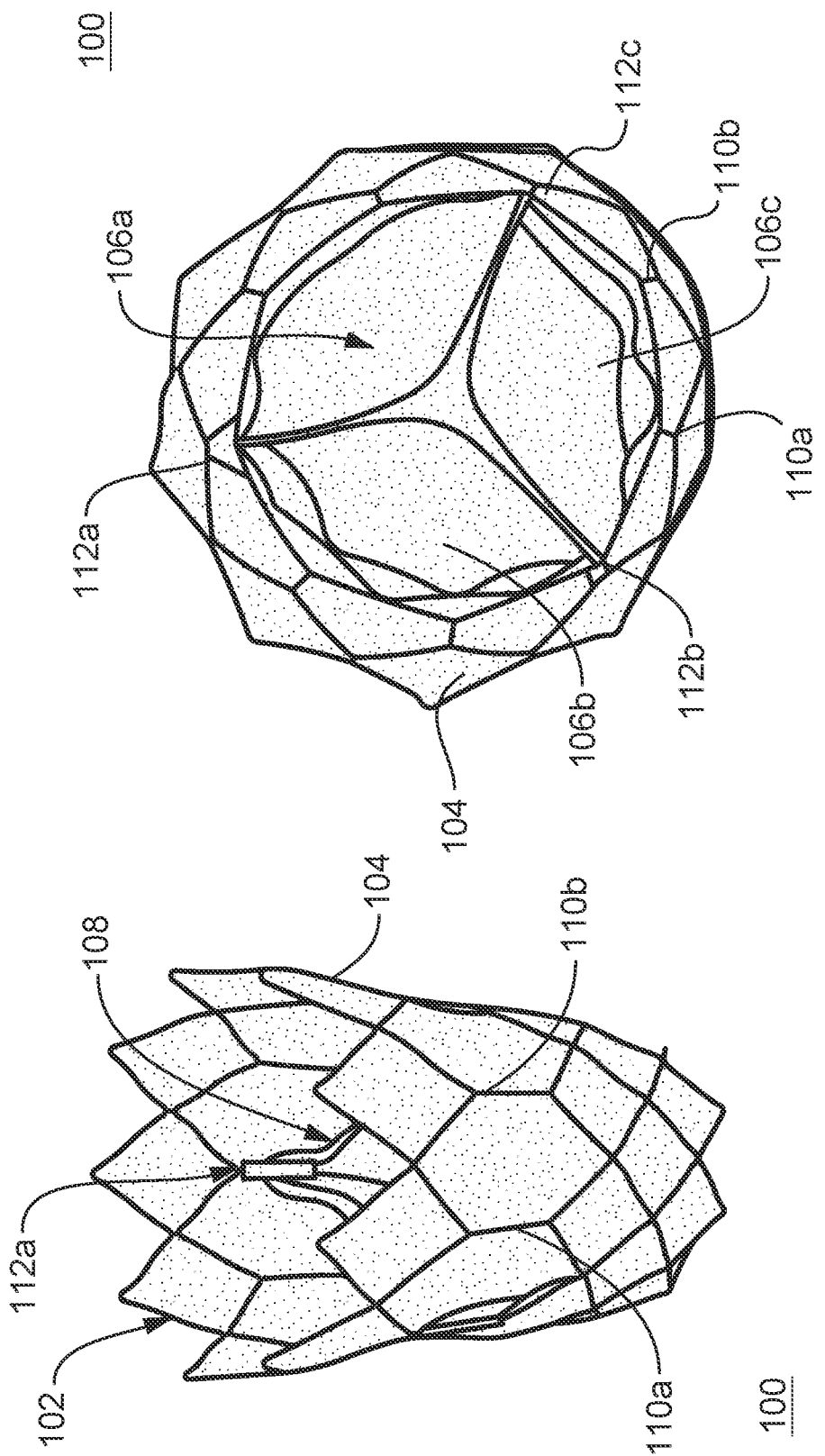
FIGS. 1A and 1B provide perspective (in which fluid flows from the bottom of the stent toward the top of the stent) and top (in which fluid flows out of the page when the valve is open and flows down into the page to close the valve) views of a valve according to an embodiment of the invention.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Aspects of the invention provide a novel platform that allows development of polymeric valves of any size and shape. Aspects of the invention can be applied to valves designed for surgical implantation (e.g., through a sternotomy or thoracotomy) or valves designed for percutaneous, transcatheter implantation. Additionally, embodiments of the invention allow for possible percutaneous replacement of a dysfunctional valve, whether in adults or in small children. In addition, if implanted in a child, embodiments of the invention allow the valve to be serially expanded to accompany the child's growth.

Cardiac Applications

Multiple types of congenital heart defects require heart valve replacement surgery in infancy or childhood. In adults, the most commonly replaced valves are aortic and mitral, whereas in children, the pulmonary valve is the most commonly replaced valve. Heart valves are currently replaced using tissue valves (homograft or xenograft) or mechanical metal valves, each having their shortcomings. Homograft valves are in short supply, particularly in sizes suitable for use in children, and biologic tissue-based valves (whether bovine, porcine, or homograft) tend to induce an immunologic reaction which leads to failure of these valves. Mechanical valves generally require anticoagulation, and are almost never used in the pulmonary position due to an increased risk of thrombosis.

Furthermore, none of the surgically implanted valves can adapt to growing patients. The rapid growth of pediatric patients leads them to outgrow their implanted valves within a few years and induces a cycle of frequent surgical valve replacements during childhood. Aspects of the invention provide valves having improved biocompatibility, durability, and hemodynamic performance and would reduce the frequency of recurrent open heart surgeries for valve replacement.

Venous Applications

Additionally, aspects of the invention can be used for venous valve replacement in patients having venous disease such as chronic venous insufficiency (leading to leg swelling). Because the polymer leaflets can be made extremely thin, the valves can even open under extremely low venous pressure gradients.

Artificial, Flexible Valves

Referring now to FIGS. 1A and 1B, one aspect of the invention provides an artificial, flexible valve 100. The valve includes an expandable, cylindrical stent 102 defining a wall 104. Valve 100 further includes a plurality of leaflets 106a-106c. Wall 104 can be formed by dip coating stent 102 in a polymer as further described herein. Leaflets 106 can be coupled to wall 104 along seams 108 (also referred to herein as "attachment line," "leaflet-stent attachment line," and "attachment seam") using a variety of approaches (e.g., glue) as discussed further herein. Stent 102 can include one or more vertical posts 110, 112, which can be relatively narrow posts 110 (also referred to herein as a "first set of posts") or relatively wide posts 112 (also referred to herein as a "second set of posts"). Preferably leaflet joints between adjacent leaflets 106 are positioned on or close to a vertical post 110, 112 of the stent 102.

The valve 100 will now be described in the context of its components and methods of fabrication.

Stents

Figure 2:
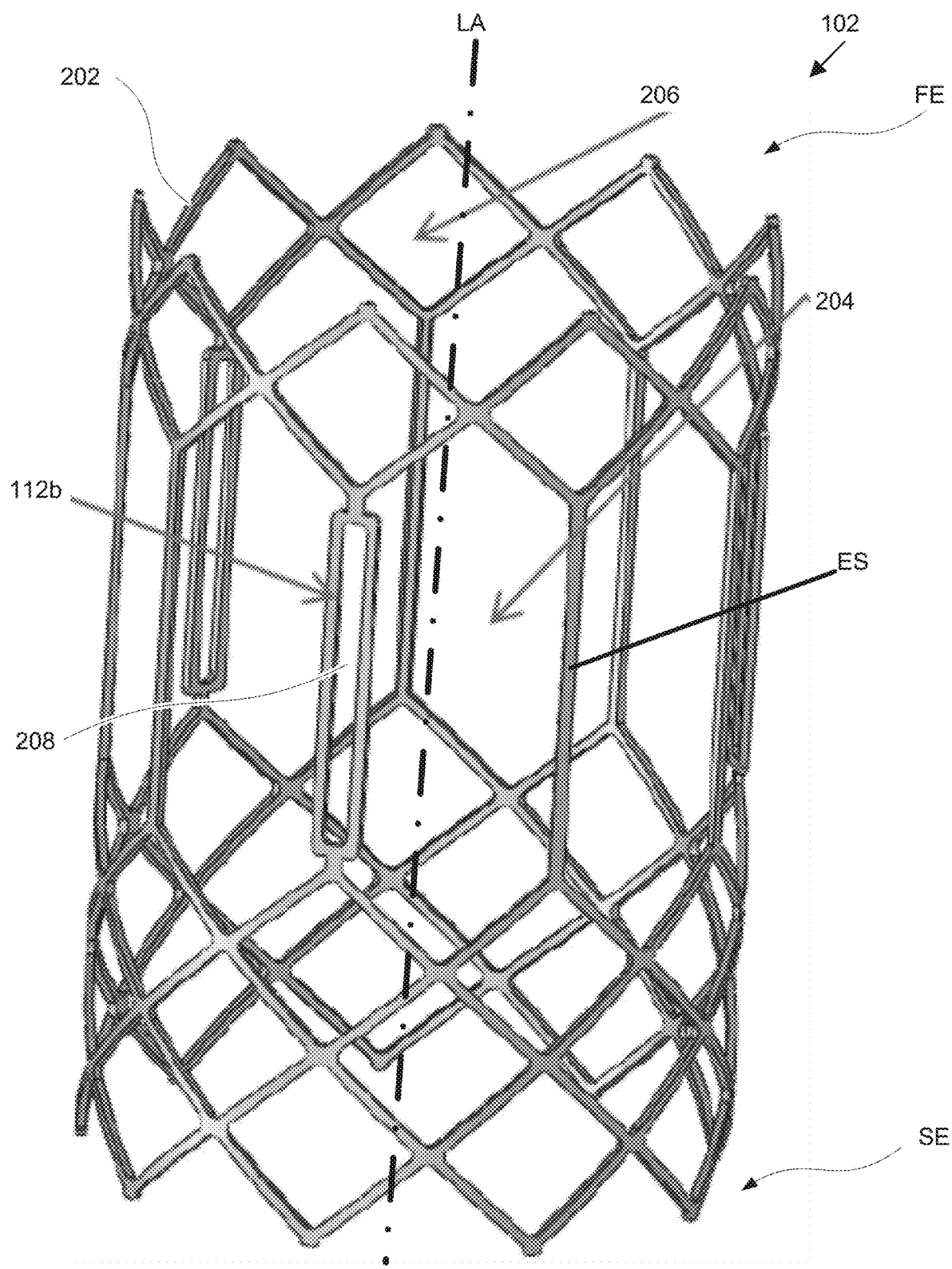
FIG. 2 depicts a stent according to an embodiment of the invention.

Referring now to FIG. 2, stent 102 can be a metallic stent having plurality of wires, strips, and the like 202 defining a plurality of cells 204, 206 of various sizes, and extending between a first open end FE and a second open end SE, and defining a longitudinal axis LA therebetween. Stent 102 can be fabricated from a variety of malleable materials such as stainless steel, 316L stainless steel, cobalt-chromium alloys, nickel-titanium alloys (colloquially known as "nitinol"), and the like. Stent 102 can also be formed from various non-metallic materials such as plastics such as polyethylene, polyurethane, polytetrafluoroethylene (PTFE), silicone, poly (propylene) (PP), polyethylene terephthalate (PET), and the like.

Stent 102 can be completely enveloped (e.g., about its external surface ES, as shown in FIG. 2) by a polymer dip coating. Stent 102 and/or wall 104 can also be fabricated from a biocompatible material.

The stent 102 can be manufactured by laser cutting or wire forming. To increase bonding strength between metal and polymer, roughness of stent surface can be controlled. Some or all open cells 204, 206 of the stent can be covered as the bare 102 stent is dipped into the polymer solution.

Figure 6:
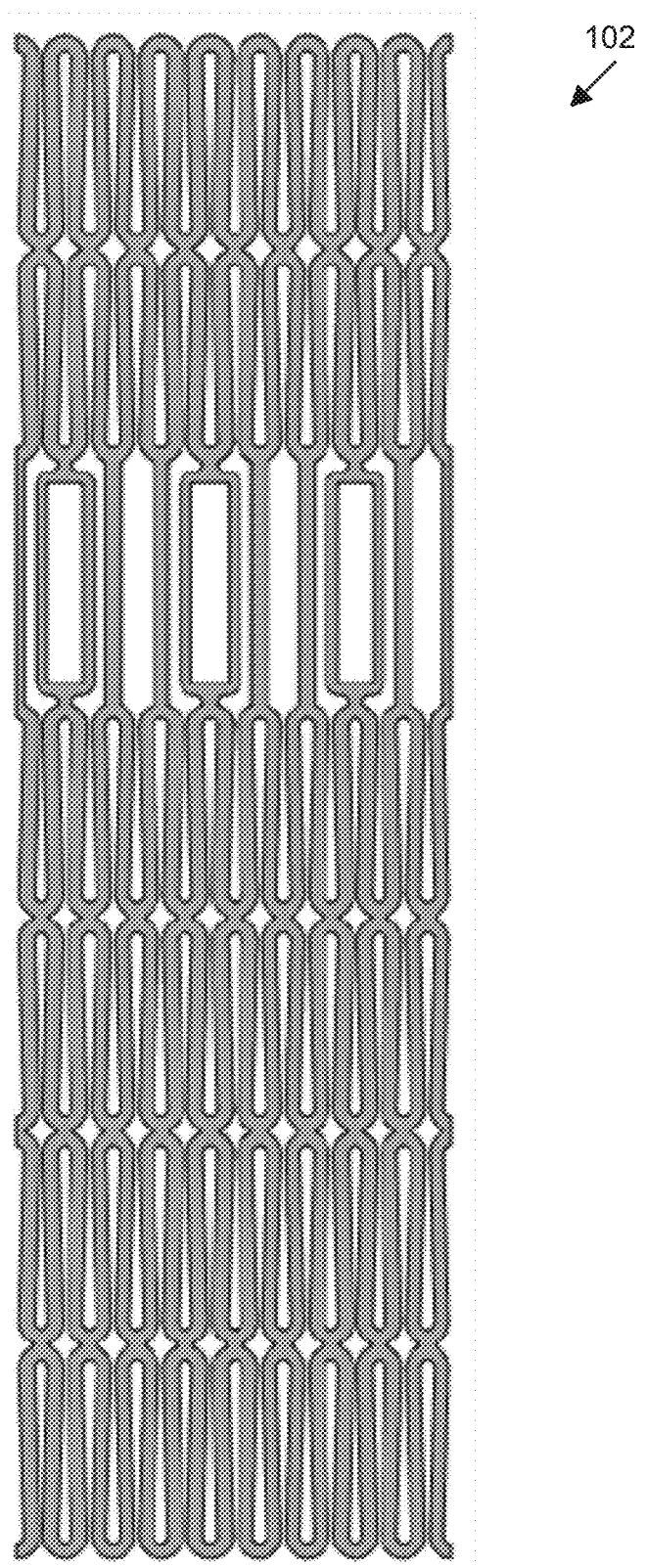
FIG. 6 depicts a stent prior to expansion, dip coating, and leaflet installation according to an embodiment of the invention.

FIG. 6 depicts a stent 102 prior to expansion, dip coating, and leaflet installation. Stents 102 typically have a diameter of between about 2 mm and 6 mm prior to expansion and can be expanded to between about 5 mm and about 30 mm for implantation into a subject.

The components of stent 102 can have a variety of dimensions that can be selected to achieve a desired flexibility, rigidity, resilience, and the like. For example, the thickness and width of components of the stent 102 can be between about 0.1 mm and about 2 mm.

As discussed above, stent 102 can include one or more vertical posts 110a-110c to enhance bonding with leaflets 106.

Stent 102 can include a plurality of vertical posts 110 that can serve a variety of functions. Some vertical posts 110 can include additional structure and are referred to herein as wide posts 112. Wide posts 112 are preferably located at leaflet joints where two leaflets 106 meet. For example, in a valve 100 having three leaflets 106, wide posts 112 can be positioned at 120° intervals within cylindrical stent 102.

Wide posts 112 provide mechanical support to leaflets and prevent or substantially limit inward deformation of wall 104 due to tensile forces applied to leaflets 106 transferred to wall 104. Without being bound by theory, it is believed that the wide posts 112 provide increased strength and resiliency due to formation of polymer wall 104 through windows 208 and around wide posts 112, thus providing cohesive holding of the polymer to itself around the stent 102 instead of relying solely on adhesive bonding of the polymer wall 104 to the stent 102.

Wide posts 112 advantageously allow for relaxed tolerances in positioning leaflets 106 relative to wide posts 112. For example, window 208 can have a width of between about 0.5 mm and about 3 nun (e.g., about 1 mm) and a height of between about 1 mm and about 10 mm (e.g., about 5 mm).

Figure 3C:
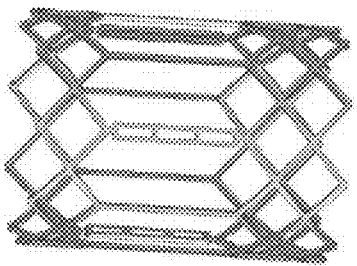
FIGS. 3A-3F depict various stent geometries according to embodiments of the invention.
Figure 3F:
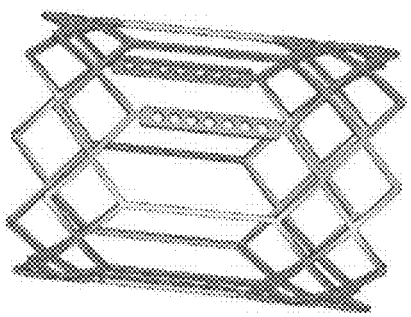
Figure 3B:
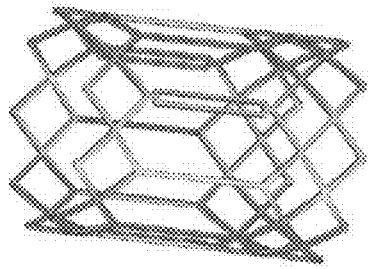
Figure 3E:
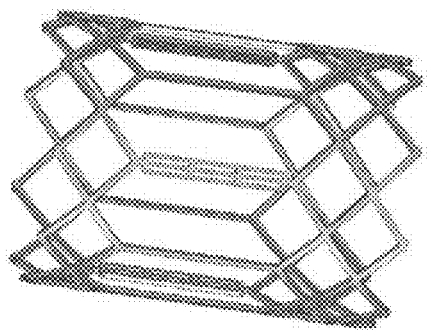
Figure 3A:
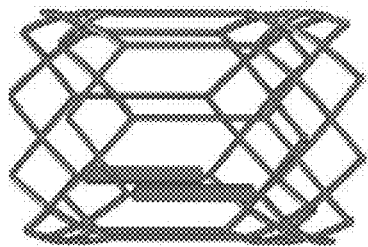
Figure 3D:
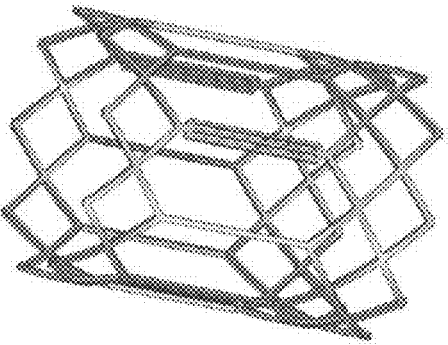

A variety of additional wide post geometries are depicts in FIGS. 3A-3F. In FIG. 3A, the wide posts have a solid architecture without any windows. In FIG. 3B, the wide posts have a substantially rectangular architecture defining a single, long window as in FIGS. 1A, 1B, and 2. In FIG. 3C, the wide posts define a plurality of coaxial substantially rectangular windows. In FIG. 3D, the wide posts define a plurality of coaxial, substantially parallel windows. In FIG. 3E, the wide posts define a plurality of coaxial, substantially rectangular windows in a 2×3 arrangement. In FIG. 3F, the wide posts include a plurality of circular windows. These wide post architectures are further depicted in FIG. 4. Although substantially circular and rectangular window geometries are depicted, any geometry can be utilized including windows having a profile approximating a triangle, a square, an n-gon (e.g., a hexagon, an octagon, and the like), and the like.

Figure 5A:
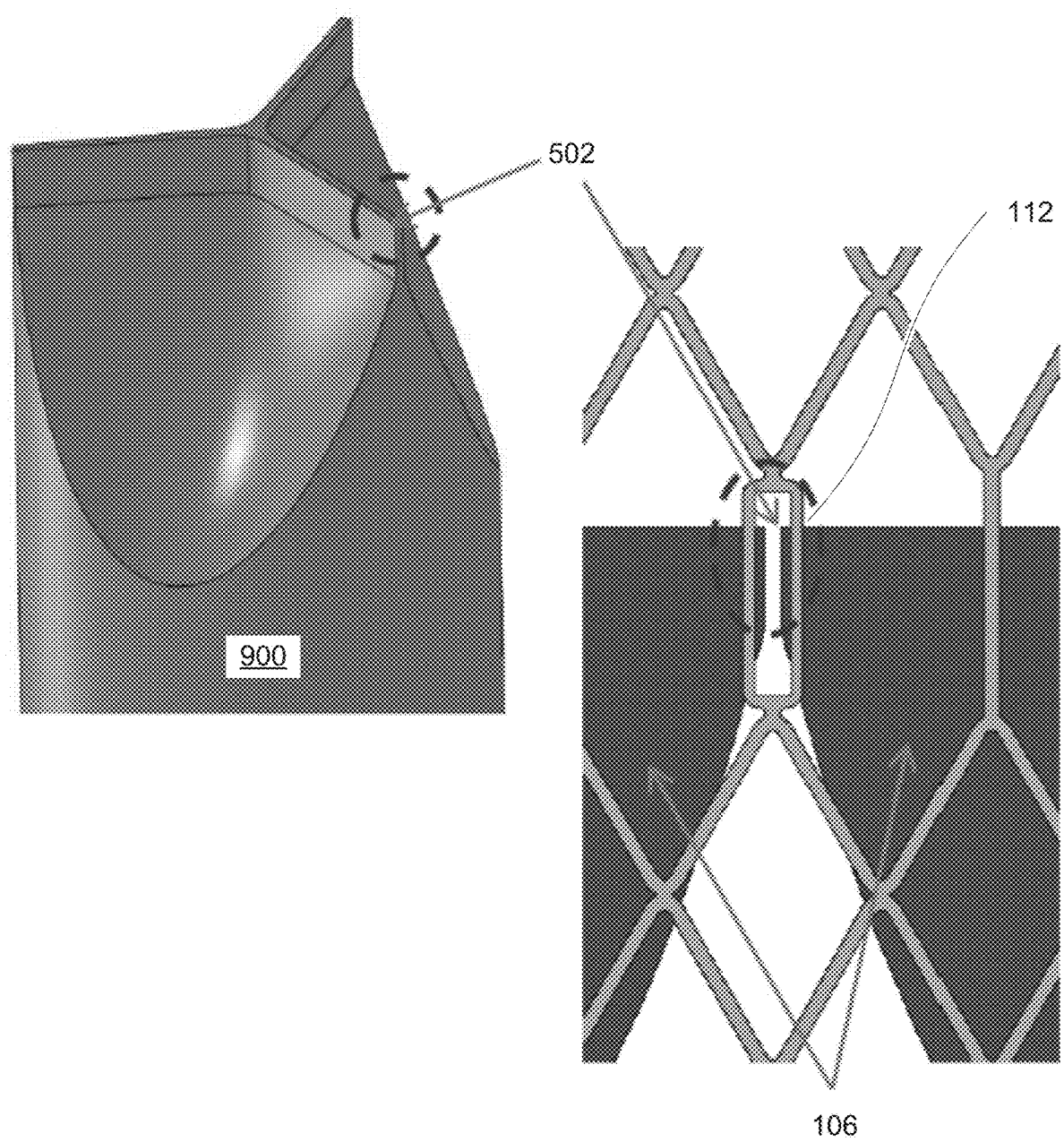
FIGS. 5A-5D depict the positioning of a leaflet joint adjacent to a window of a vertical post according to an embodiment of the invention.
Figure 5B:
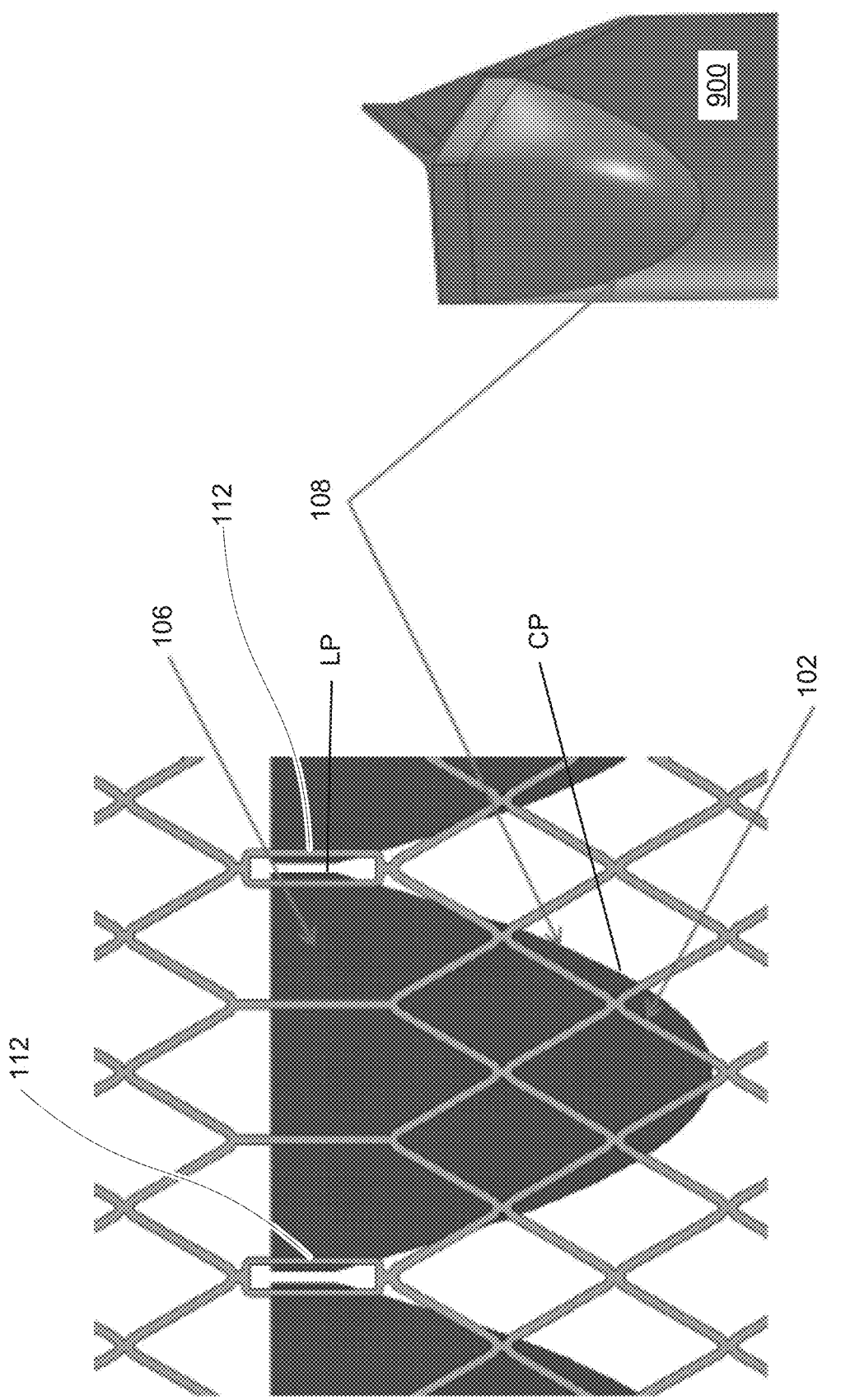
Figure 5D:
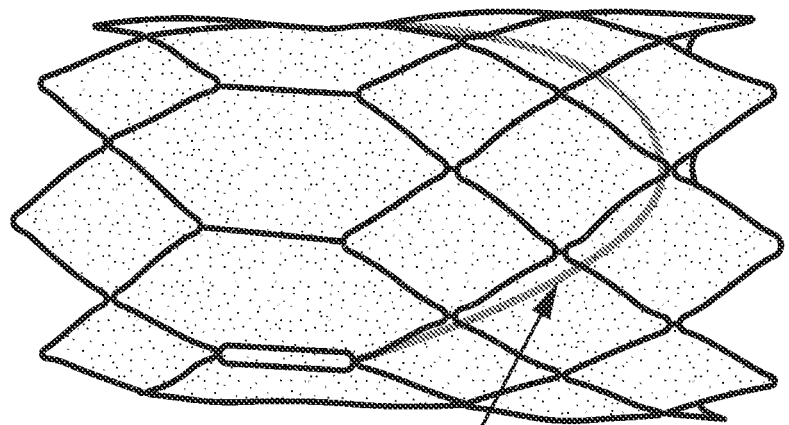
Figure 5C:
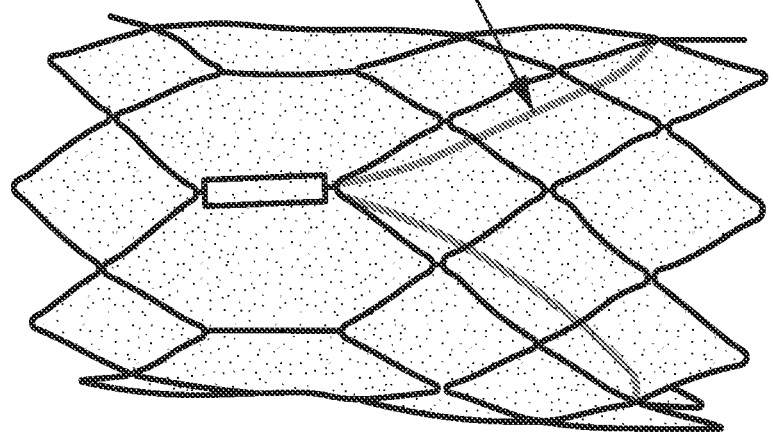

Referring now to FIGS. 5A-5D, the positioning of a leaflet joint 502 (formed, e.g., on mandrel 900 as discussed herein) adjacent to window 208 of wide post 112 is depicted. (The polymer dip-coated wall 104 is completely transparent for case and clarity in viewing, but can be transparent, translucent, or opaque.) FIG. 5B-5D further depict how a geometry of the stent 102 can be selected to substantially approximate the leaflet-stent attachment seam 108 discussed herein in order to provide added mechanical support and resiliency.

Figure 7:
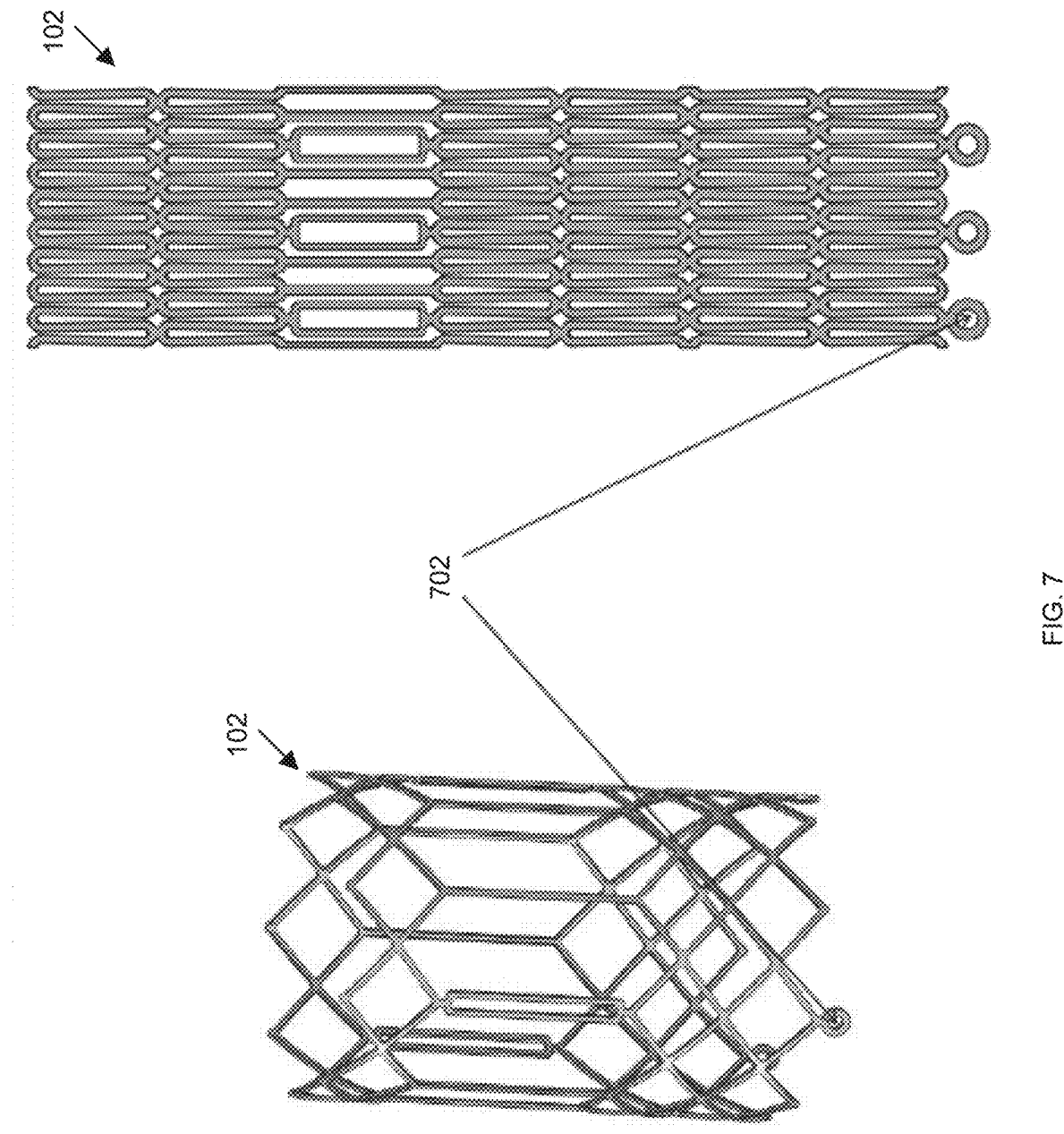
FIG. 7 depicts a stent including one or more anchor points according to an embodiment of the invention.

Referring now to FIG. 7, stent 102 can include one or more anchor points 702. Anchor points 702 advantageously facilitate holding, dipping, and rotation of the stent 102 during the dip coating process without interfering with the dip coating of the remainder of the stent architecture. Accordingly, the entire stent 102 can be dip coated in a single dipping, although multiple dippings can be utilized to control coating density, thickness, and the like. Anchor points 702 can also receive one or more radio-opaque materials such as platinum to aid in placement and visualization of the valve.

Figure 8:
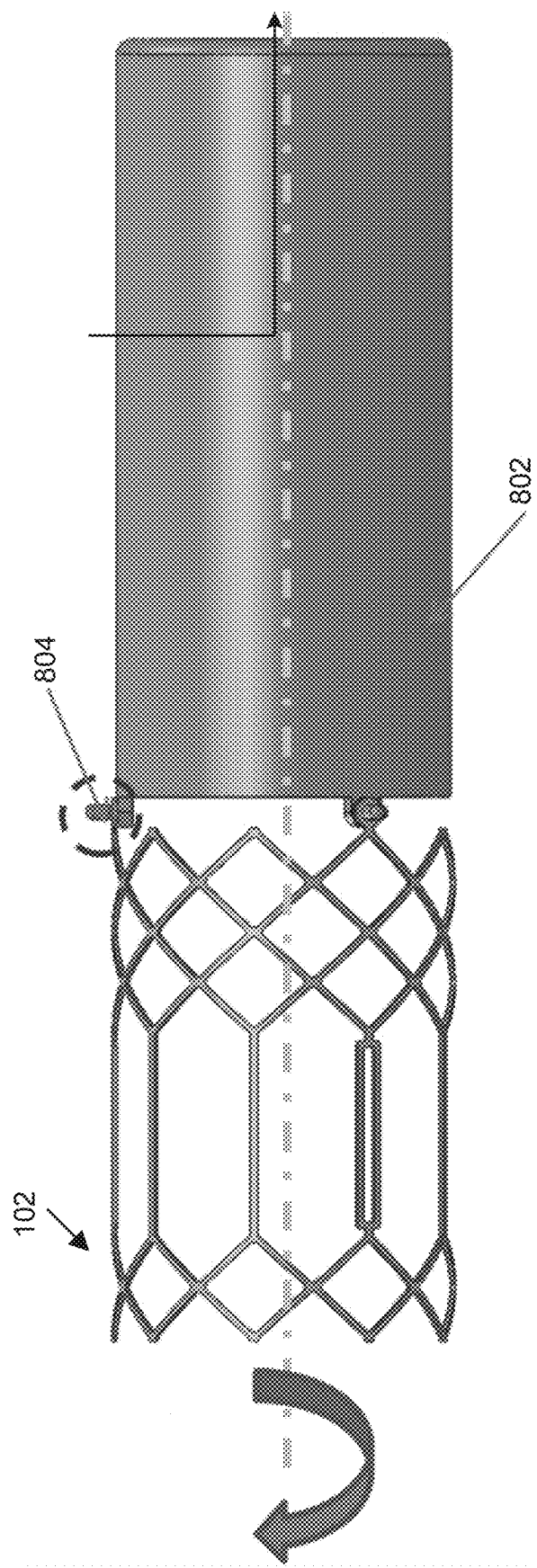
FIG. 8 depicts the engagement of a stent with a holder for dipping and rotation according to an embodiment of the invention.

In one embodiments depicted in FIG. 8, stent 102 can be engaged with a holder 802 (e.g., by posts 804) for dipping and rotation. Once the polymer (again depicted as, but not necessarily, transparent) is wet on the stent 102, the stent can be positioned horizontally and rotated axially.

Leaflets

Leaflets 106 can be formed using a variety of techniques including dip coating, 3D-printing (also known as additive manufacturing), molding, and the like.

Figure 9A:
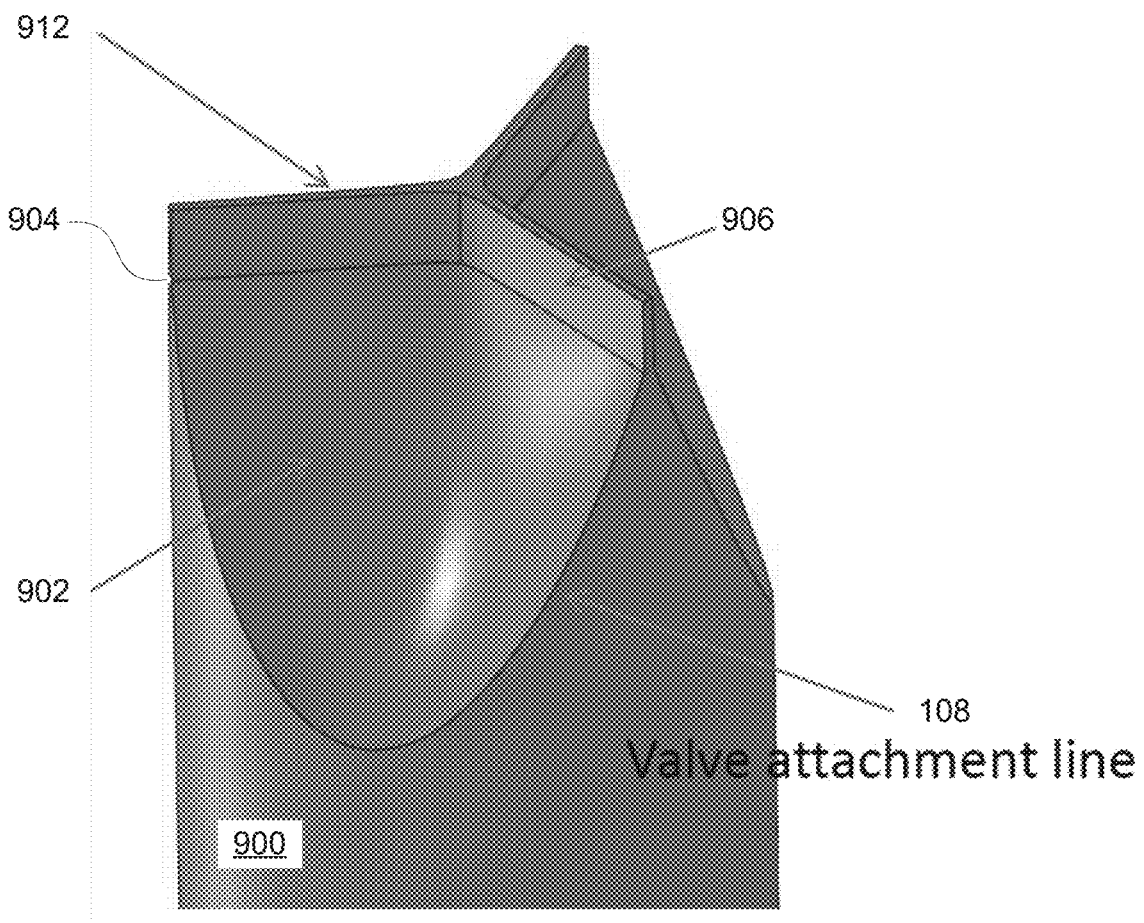
FIGS. 9A-9E depict a mandrel according to an embodiment of the invention.

Referring now to FIG. 9A, leaflets 106 can be fabricated by dip coating a mandrel 900 with a polymer. The mandrel 900 can be made with a solid such as a metal (e.g., stainless steel, titanium, aluminum, and the like), a plastic (e.g., polyethylene, polypropylene, polyvinyl chloride, polytetrafluoroethylene, polyoxymethylene, and the like), and the like. Since the coated polymer leaflets 106 will be removed from the mandrel 900 after the polymer dries, roughness of mandrel surface can be controlled using known machining and other manufacturing techniques. The mandrel 900 can be made from a cylinder. Preferably, the diameter of the mandrel 900 is a slightly (e.g., between about 0.05 and about 0.4 mm) smaller than inner diameter of stent 102 after expansion.

The mandrel 900 for the leaflets 106 can have novel features, including edges representing the leaflet attachment points that are mathematically defined and leaflet tips that are extended in order to increase the coaptation length of the leaflets (including a curved portion CP and a linear portion LP, as shown in FIG. 9A). The mandrel 900 can be dimensioned to produce leaflets 106 having different regional thickness and supplementary materials such as directional fibers or reinforcing particles inserted between layers or mixed into the polymer solution in order to increase durability. For example, polymer interaction with particles on the nanoscale or microscale can greatly improve the physical properties or tear resistance of the polymer leaflets 106.

Mandrel 900 can be designed to have a complementary geometry to the desired leaflet shape and permits easier viewing of leaflet geometry. Although mandrel 900 is utilized to describe the geometry of the leaflet 106, it should be recognized that the upstream surface of the resulting leaflets will have this geometry when formed by dip coating and that the complementary geometry of the leaflet(s) 106 can be produced using techniques other than dip coating. Mandrel 900 is preferably cylindrical and can have an outer profile substantially approximating an inner profile of stent 102. Mandrel 900 can define a plurality of pockets 902 that each define a leaflet 106 as it hangs from wall 104 via attachment line 108. Each leaflet 106 terminates in a commissure line 904 often, but not necessarily lying in a plane at the point where the elliptical or parabolic curve ends and where the leaflet often contacts the other leaflets. A substantially vertical coaptation region 906 can extend beyond the commissure line 904 to an extended commissure line 912 for improved sealing as will be discussed herein.

Figure 9C:
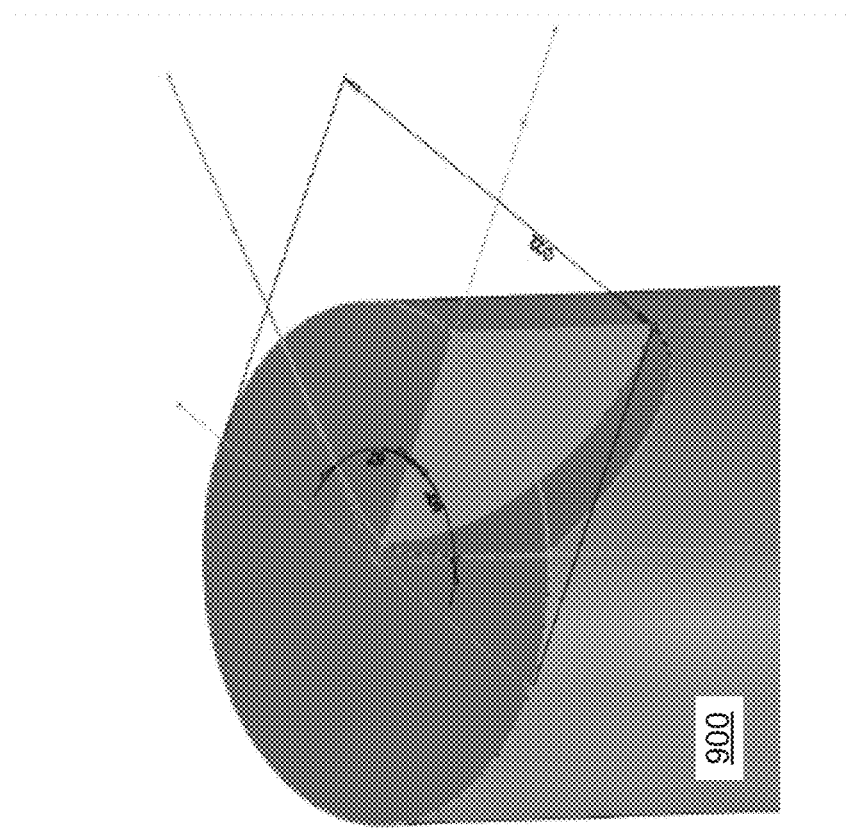
Figure 9B:
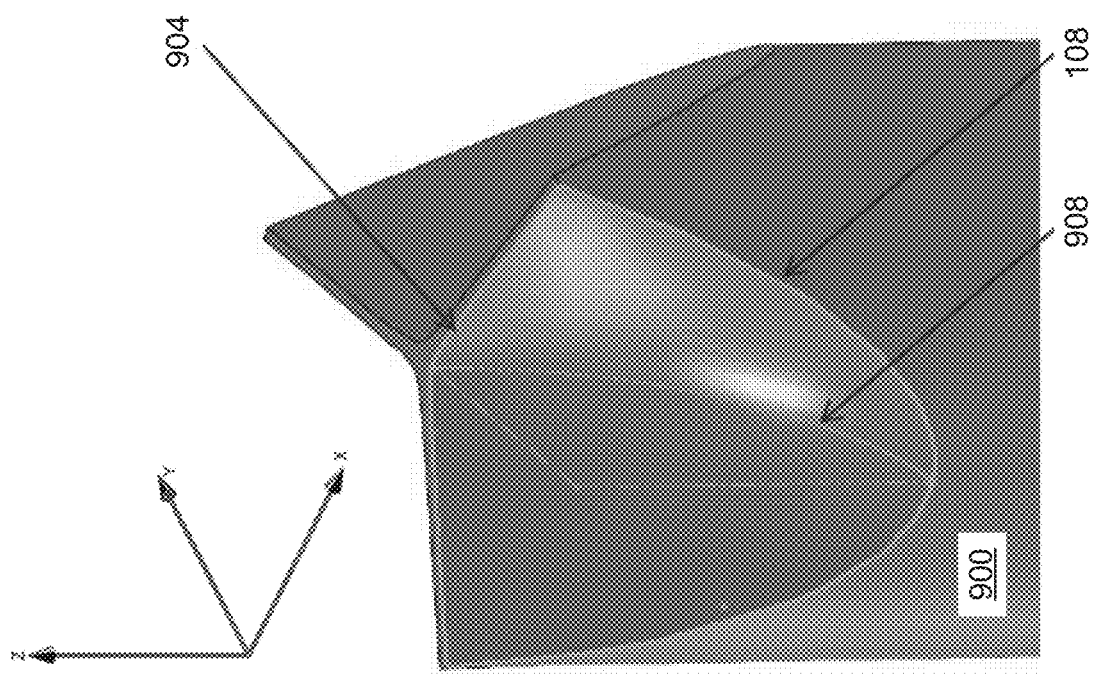
Figure 10C:
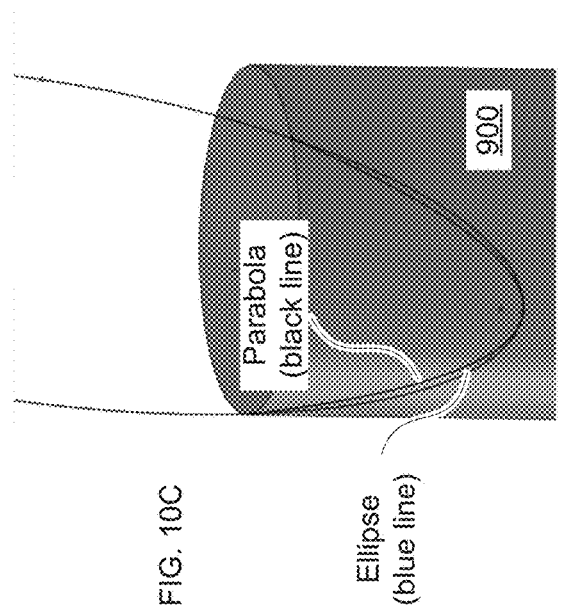
FIGS. 10B and 10C depict a comparison of elliptical vs. parabolic leaflet stent attachment lines according to embodiments of the invention.
Figure 10B:
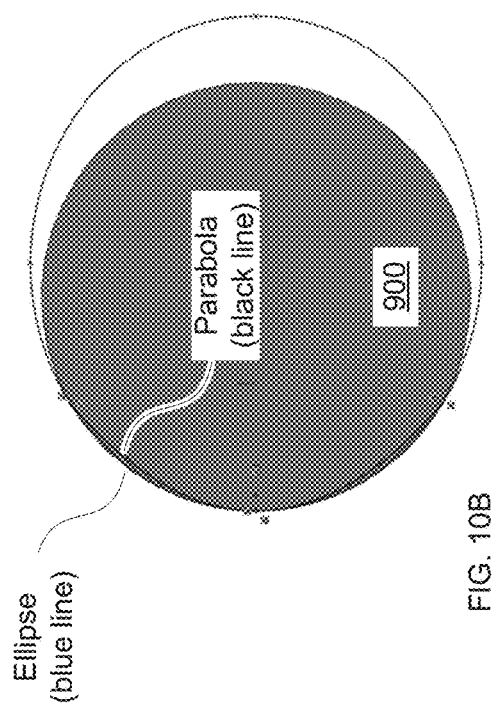
Figure 10A:
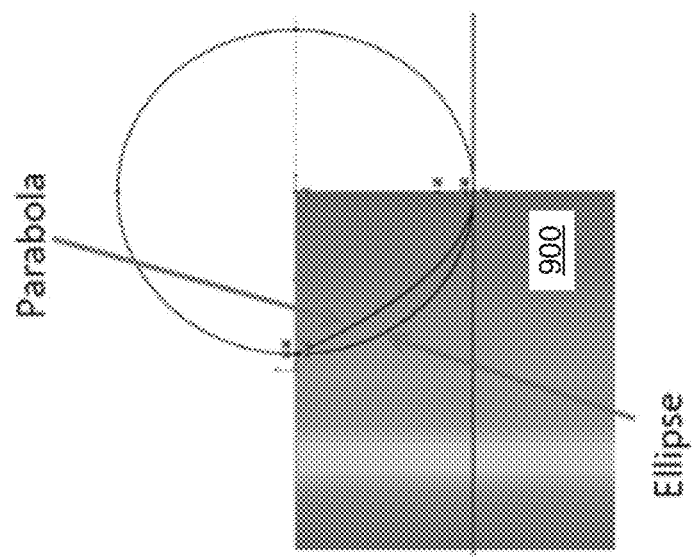
FIG. 10A depicts a comparison of elliptical vs. parabolic geometries leaflet valley lines according to embodiments of the invention.

Referring now to FIGS. 9B and 9C, mandrel can be cast, machined, printed, or otherwise fabricated so that pockets 902 have a desired geometry. In one embodiment of the invention, the commissure line 904 (and optionally the coaptation region 906 and extended commissure line 912) has a substantially hyperbolic profile when viewed in the x-y plane. Additionally or alternatively, leaflet-stent attachment line 108 and/or a leaflet valley line 908 (formed by taking a cross-section in a z plane) can have substantially elliptical profiles. Although other quadratic profiles (e.g., parabolic) could be used, elliptical profiles better promote a secure pocket shape and the closure of the leaflet-stent attachment line 108 to the contour of the cylindrical mandrel 900. A comparison of elliptical vs. parabolic leaflet valley lines is provided in FIG. 10A. A comparison of elliptical vs. parabolic leaflet-stent attachment lines is provided in FIGS. 10B and 10C.

Figure 9D:
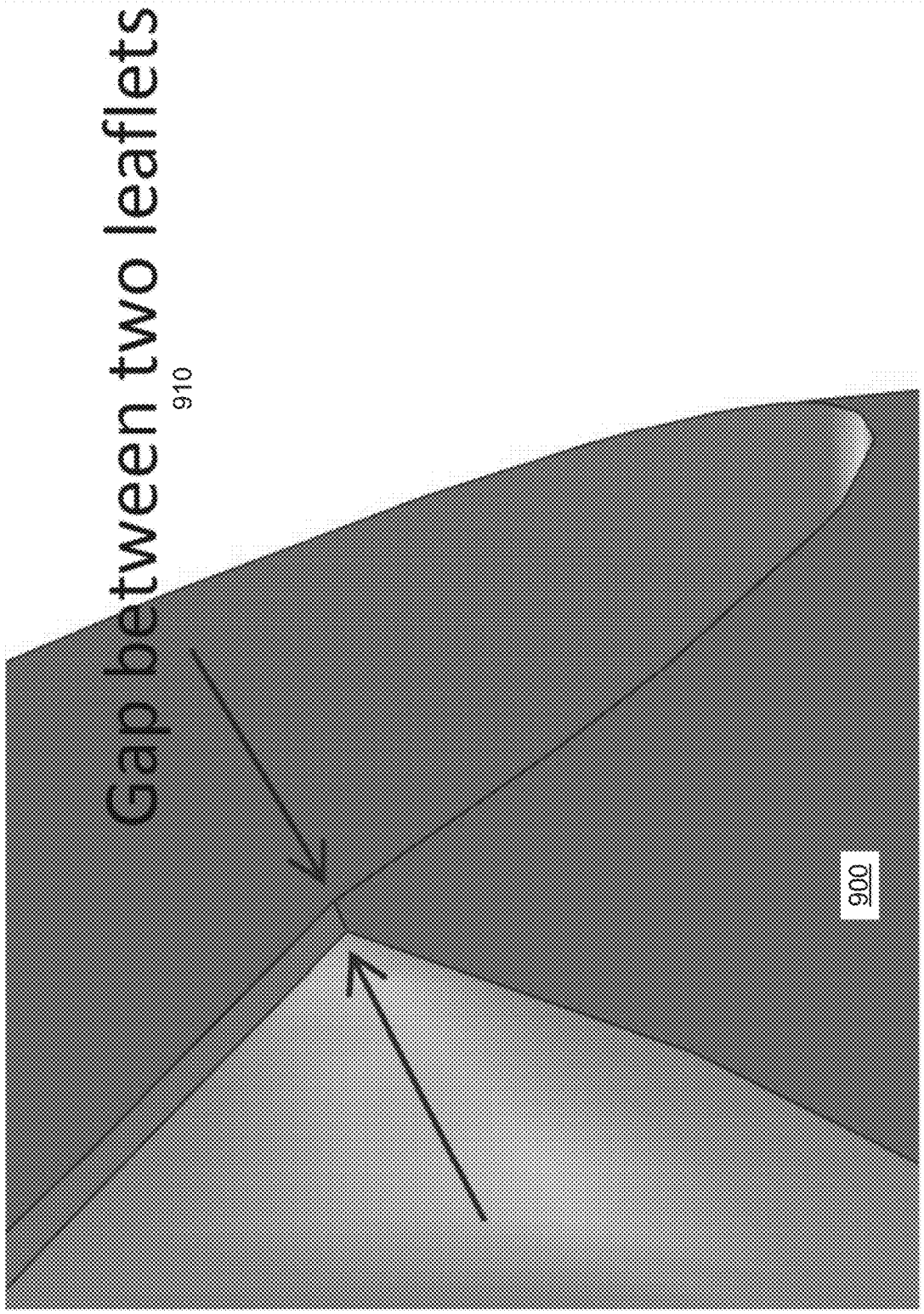

Referring now to FIG. 9D, mandrel 900 can define a gap 910 between adjacent leaflets. Advantageously, leaflets 106 with a hyperbolic profile can produce smaller gaps than leaflets with parabolic profiles. For example, gaps 910 can be less than 1 mm or between about 0.1 mm and about 1 mm (e.g., between about 0.1 mm and about 0.2 mm, between about 0.2 mm and about 0.3 mm, between about 0.3 mm and about 0.4 mm, between about 0.4 mm and about 0.5 mm, between about 0.5 mm and about 0.6 mm, between about 0.6 mm and about 0.7 mm, between about 0.7 mm and about 0.8 mm, about 0.8 mm and about 0.9 mm, about 0.9 mm and about 1 mm, and the like).

Figure 9E:
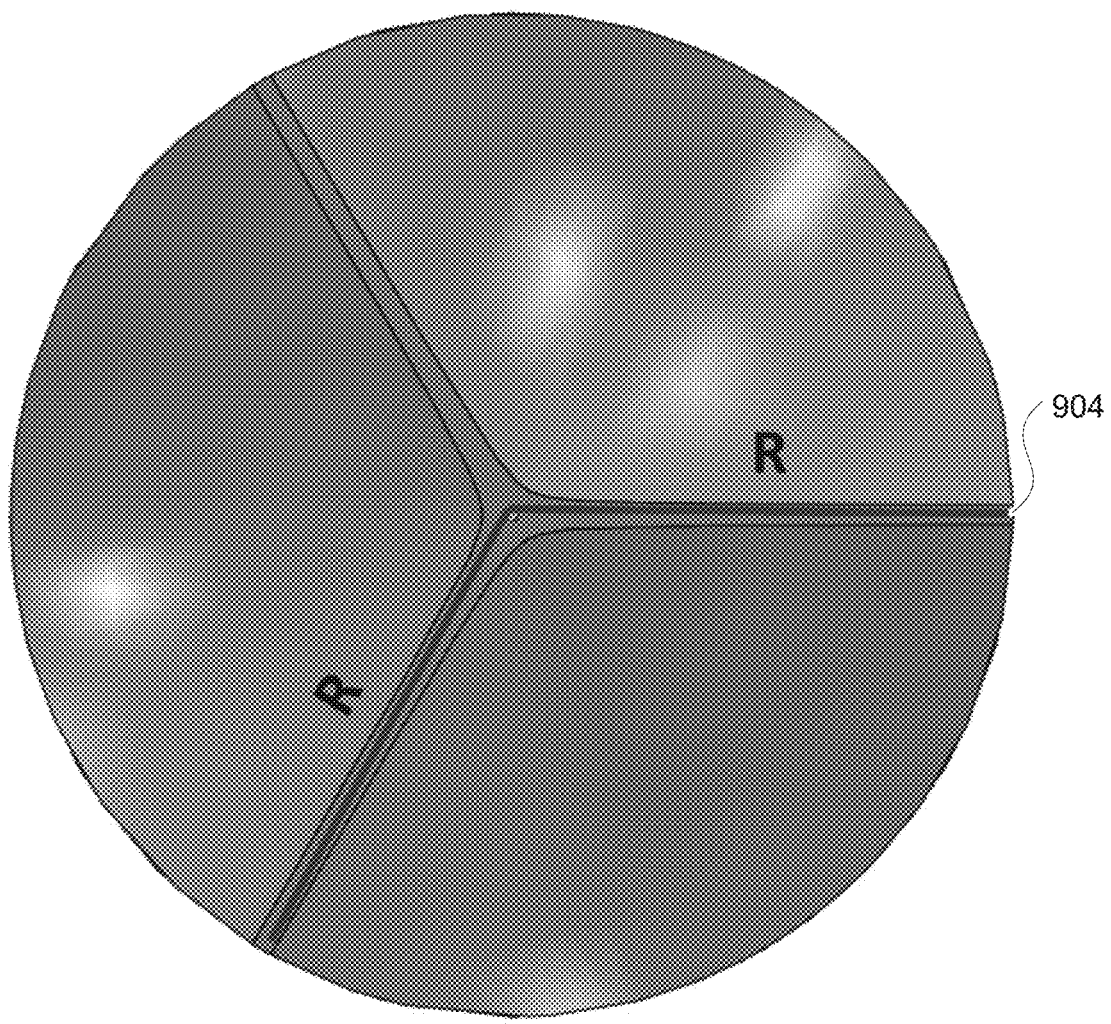
Figure 9F:
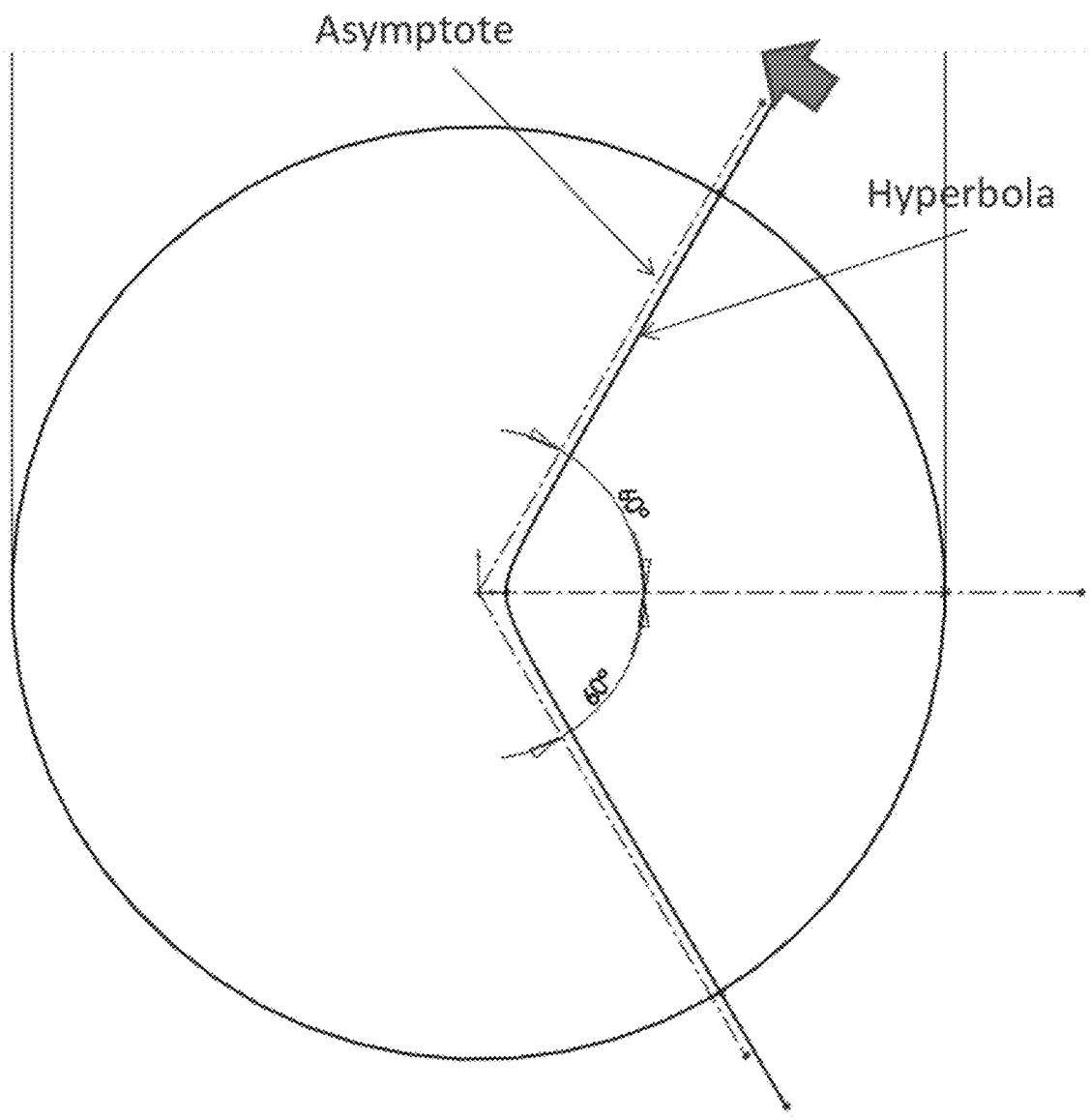
FIG. 9F depicts the positioning of a hyperbolic commissure line relative to defined asymptotes according to embodiments of the invention.

As seen in FIG. 9E, the length of hyperbolic commissure line 904 is about twice the radius of the stent or mandrel. The positioning of a hyperbolic commissure line 904 relative to defined asymptotes is depicted in FIG. 9F.

Referring now to FIG. 11A, coaptation region can have minimal height in the z-axis so as to consist only of the commissure line 904. Alternatively, coaptation region 906 can have a vertical extension in the z-axis to an extended commissure line 912 as depicted in FIGS. 11B-11D. The height of the coaptation region 906 can be selected to reduce the amount of regurgitation, while still allowing the valve to open. For example the coaptation region 906 can have a height between about 1 mm and about 10 mm (e.g., about 3 mm). Although FIGS. 11B-11D depict extensions of coaptation region 904 that extend solely in the z-axis, the same effect can be achieved using a smooth leaflet-stent attachment line that extends in the z-axis so that the adjacent leaflet-stent attachment lines (and/or the regions of leaflets hanging therebetween) approach and/or contact each other to form an extended coaptation region.

The zone of coaptation is affected by the pressure placed upon the closed valve 100. The higher the pressure, the more downward tension is placed on the leaflets 106, possibly leading to a failure of coaptation with consequent regurgitation. Proper coaptation also allows the leaflets 106 to support each other, so there is less stress placed on any individual leaflet 106. Another benefit of enhancing height of the coaptation zone is that this allows the valve 100 to be re-dilated to a larger diameter late after implantation (such as to accommodate growth of a pediatric patient), while still maintaining competence of the valve 100.

Options for enhancing the height of the coaptation zone include creating excess length of the leaflet free edges, so that the free edge length is greater than twice the radius of the stent or mandrel depicted in FIG. 9E. Lengthening of the leaflet free edges can be accomplished by curved edges in the x-y plane, or in the z-axis, or in all 3 axes.

Referring now to FIGS. 12A-12D, coaptation regions 906 can have varying heights in the z-axis between the commissure line 904 and extended commissure line 912. For example, the height of coaptation region 906 can increase toward the outside of the mandrel as depicted in FIG. 12B. In another embodiment, the height of the coaptation region 906 can dip to form a trough between the outside and the center of the mandrel 900 as depicted in FIG. 12C.

Referring now to FIGS. 12E-12H, the same profiles can be applied to commissure line 904 without any coaptation region 906.

Figure 12K:
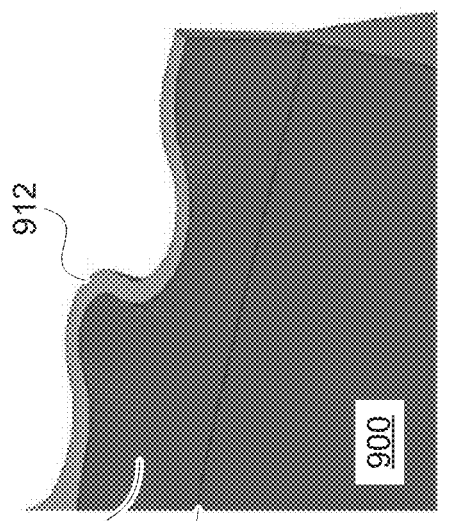
FIGS. 12I-12K depict mandrels for forming coaptation regions having curved profiles in an x-y plane, resulting in increased coaptation length, according to embodiments of the invention.
Figure 12J:
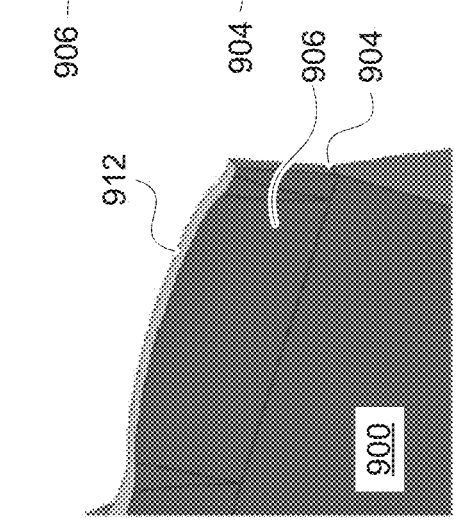
Figure 12I:
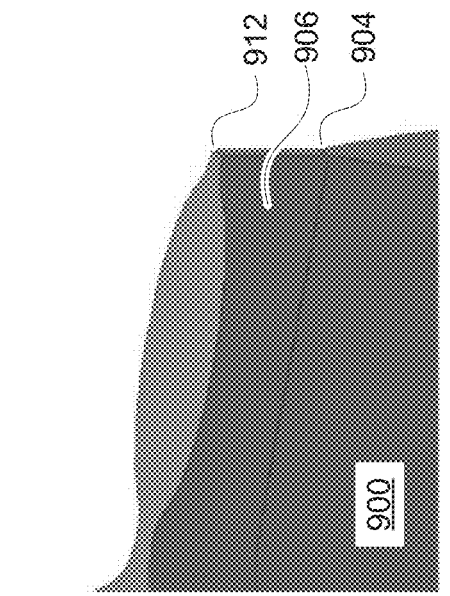

Referring now to FIGS. 12I-12K, the commissure lines 904, coaptation regions 906 and/or extended commissure lines 912 can have curved profiles in an x-y plane (as opposed to a substantially hyperbolic profile) in order to increase the length of the commissure line 904, coaptation region 906, and/or extended commissure line 912. For example, the mandrel 900 can be thicker between the perimeter and the center as depicted in FIG. 12I to produce one or more scallops. In FIGS. 12J and 12K, the mandrel 900 can have either a single curve or multiple curves.

Figure 12N:
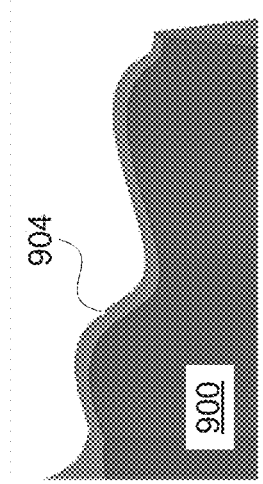
FIGS. 12L-12N depict mandrels for forming commissure lines having curved profiles in an x-y plane, resulting in increased coaptation length, according to embodiments of the invention.
Figure 12M:
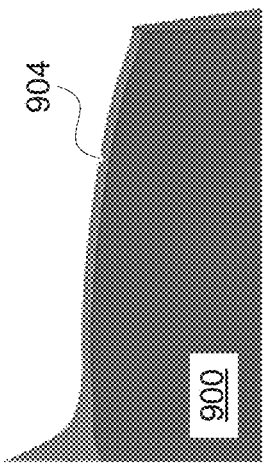
Figure 12L:
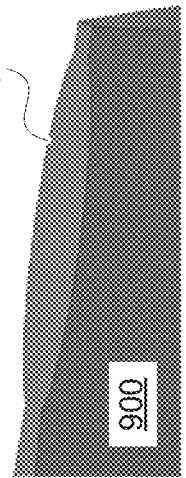

Referring now to FIGS. 12L-12N, the same profiles can be applied to commissure line 904 without any coaptation region 906.

In order to increase tear-resistance of the leaflets 106 and enhance bonding strength between leaflets 106 and stent 102, the thickness of the leaflets 106 can be controlled regionally. Because the most common failure points are at the outer edges of the leaflets 106 (such as commissure line 904 or extended commissure line 912 and leaflet-stent attachment line 108), increased thickness at outer areas of the leaflets 106 can improve the strength and durability. Also, if local areas are expected to have concentrated stress, the areas can be locally reinforced (e.g., made thicker than other areas). The thickness can be smoothly increased. The width of thickened area along leaflet-stent attachment line 108 can be large enough to cover the glued area for bonding the leaflets 106 and the covered stent 102. In some embodiments, the thickness of thickened areas of the leaflets is between about 0.1 mm and about 1 mm.

Multiple dippings can be performed to produce leaflets with a desired thickness. In some embodiments, the thickness of the leaflets is between about 0.01 mm and about 0.2 mm.

Different reinforcing materials such as strips, fibers and particles can be placed between the layers, or directly mixed into the polymer solution. The inserted material(s) can prevent tearing and reduce propagation of the tear if it occurs. The materials can have directional properties and can be layered onto, or embedded into, the leaflets in an optimal direction to prevent or limit tears.

Figure 13A:
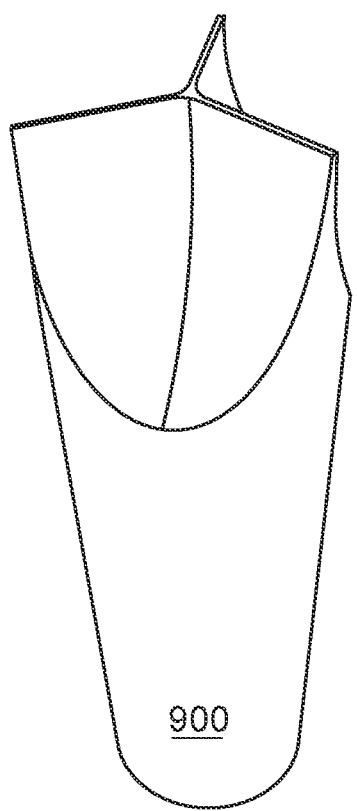
FIG. 13A depicts a mandrel according to an embodiment of the invention.
Figure 13B:
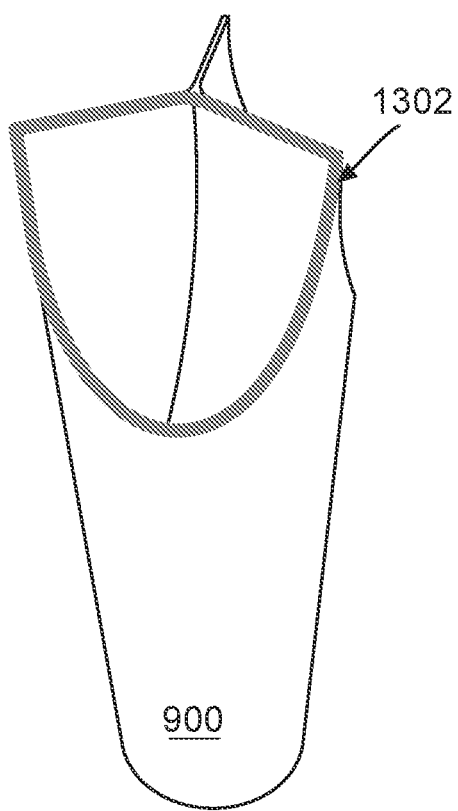
FIGS. 13B and 13C depict the positioning of reinforcing zones on a mandrel according to an embodiment of the invention.
Figure 13C:
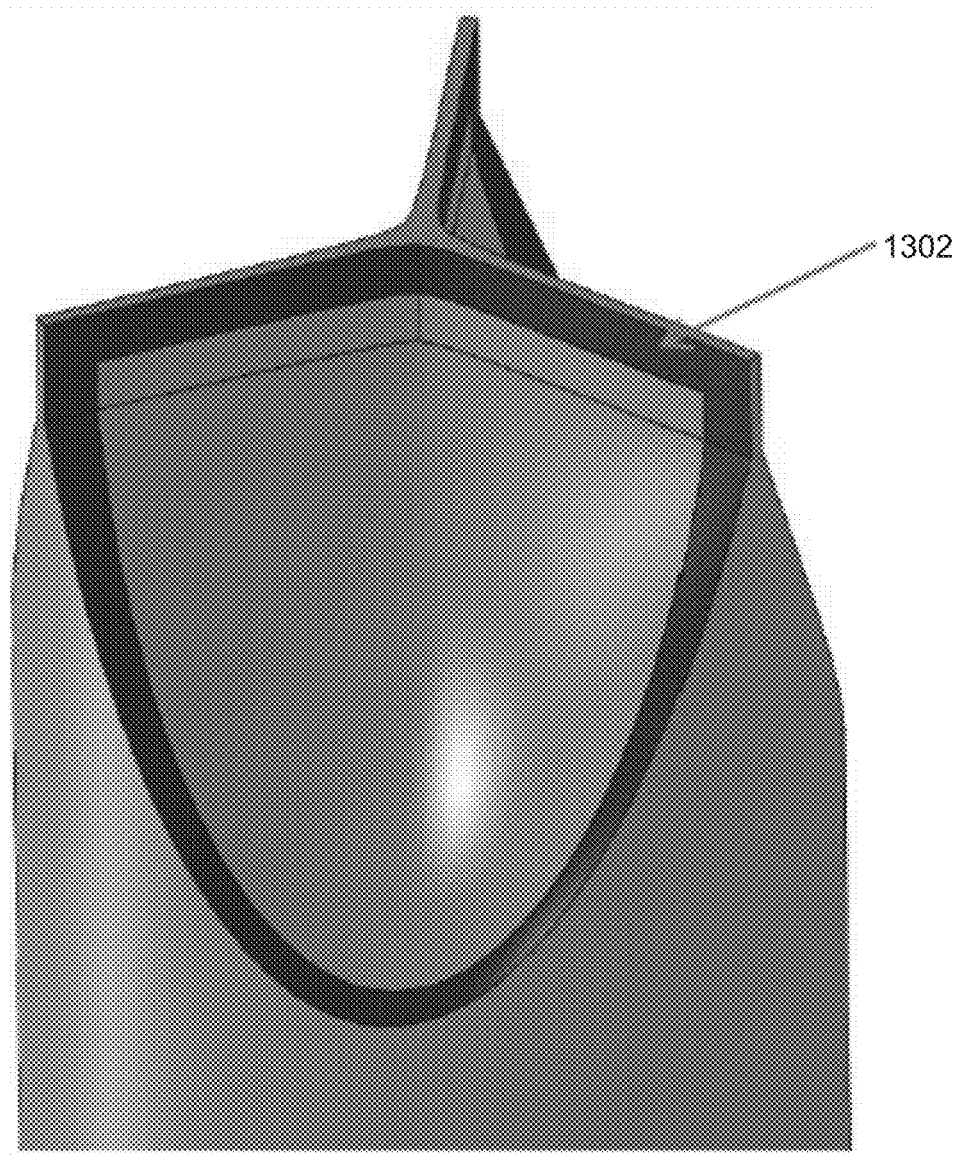

Referring now to FIG. 13A, a photograph of a mandrel 900 is provided. Referring now to FIG. 13B, a reinforcing zone 1302 can be formed on the mandrel 900 prior either by removing mandrel material to allow for additional thickness in certain (e.g., outer) regions of leaflets 106 or by introducing one or more reinforcing fibers prior to, during, or after dip coating. Suitable reinforcing materials include fibers (e.g., polymers, nanotubules, aramids, para-aramids, and the like), wires, and the like. Transitions between reinforced and non-reinforced areas can be smooth in order to minimize any turbulence in the implanted valve 100.

After dipping the mandrel 900 into the polymer solution, the coated polymer dries in order to form the leaflet(s) 106. Because the formed leaflets 106 are connected, they need to be separated from each other. These can be cut by a sharp cutter (e.g., a knife, a scalpel, a razor blade, a utility knife, and the like), a heated iron, a laser, a rotary tool, and the like. A guide on the top surface of the mandrel for cutting provides a clear, easy, and safe cutting path. The guide can be grooved/concave or convex. Also, the commissure edges of the mandrel can be sharp like a blade to facilitate leaflet separation and to improve on the quality of the cut edges.

Figure 14C:
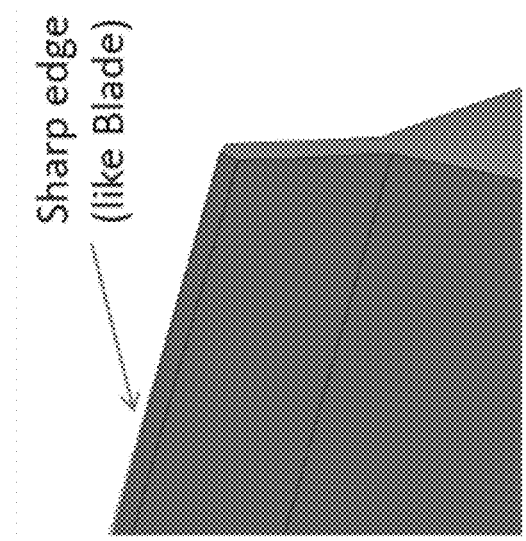
FIGS. 14A-14C depict various top profiles according to an embodiment of the invention.
Figure 14B:
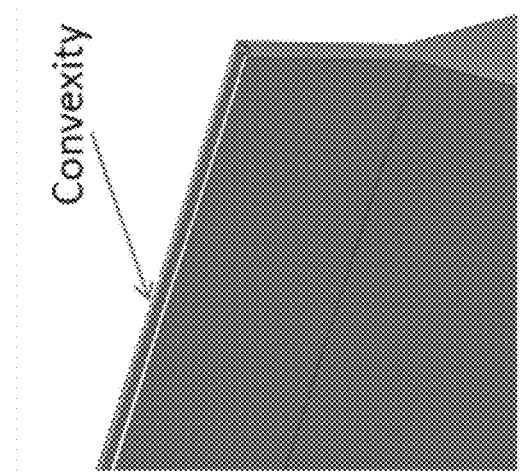
Figure 14A:
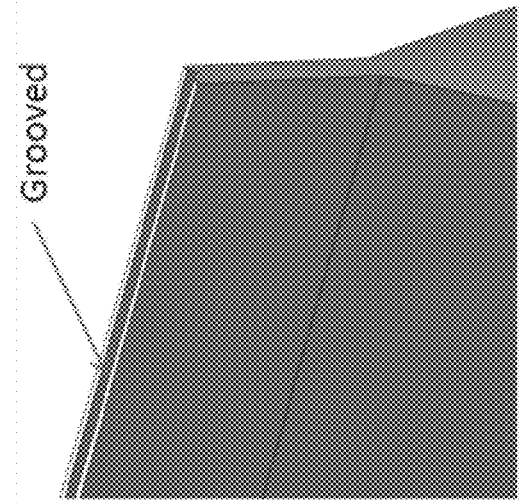

Referring now to FIG. 14A-14C, the gap portion 910 of the mandrel can have various top profiles to facilitate sealing of the leaflets and/or separation of the leaflets prior to removal from mandrel 900. For example, the gap portion 910 can have a grooved profile as depicted in FIG. 14A, a concave profile as depicted in FIG. 14B, or an angled profile as depicted in FIG. 14C. Additionally or alternatively, a heating element (e.g., an Ohmic or resistive heating element such as a wire) can be included in the mandrel and can be actuated to melt the polymer to separate the leaflets and/or relax the polymer to facilitate removal of the leaflets from the mandrel 900.

The stent-mounted valve 100 can be implanted with smaller diameter than its manufactured diameter for reducing leakage and improving durability.

Methods of Fabricating Valves

Figure 15A:
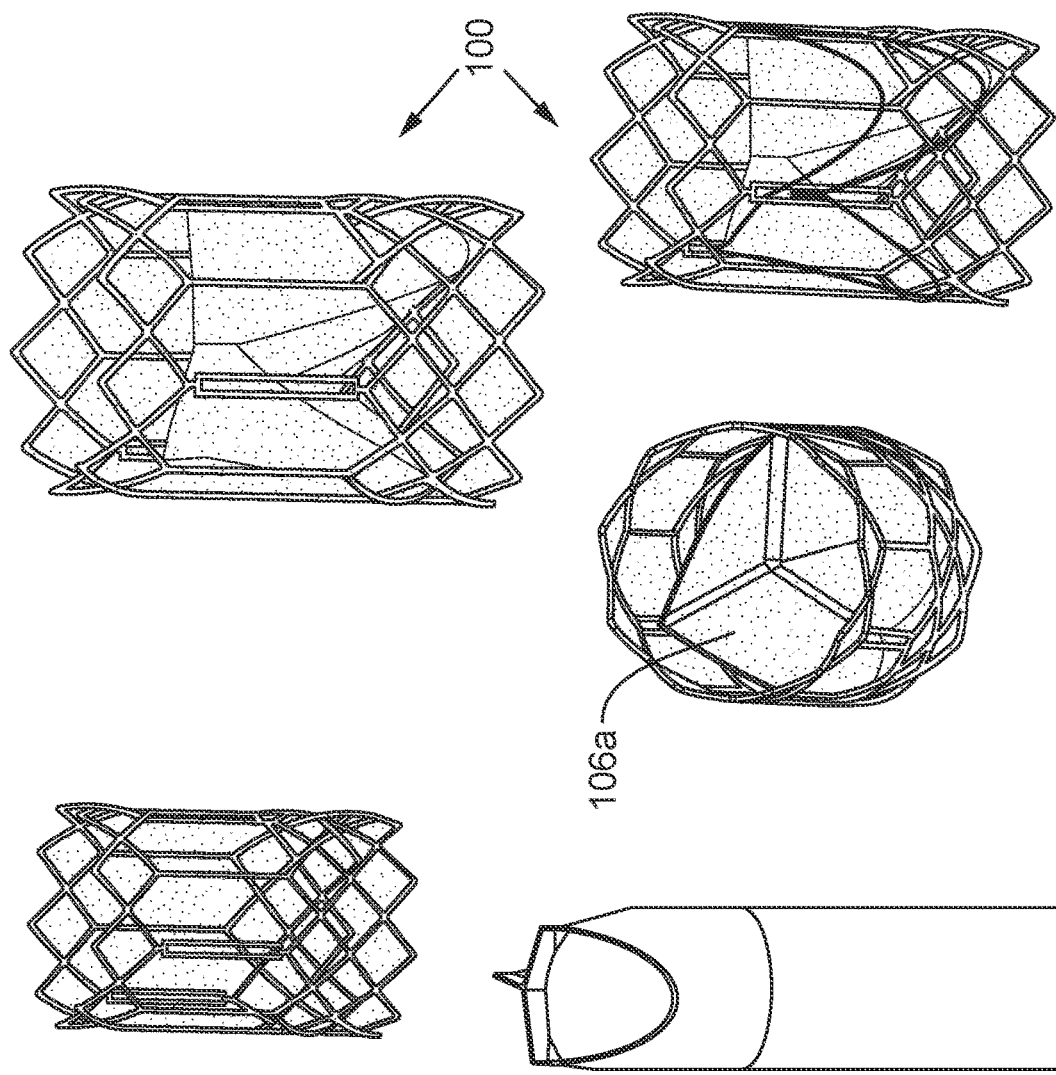
FIGS. 15A and 15B depict the fabrication of valves according to embodiments of the invention.
Figure 15B:
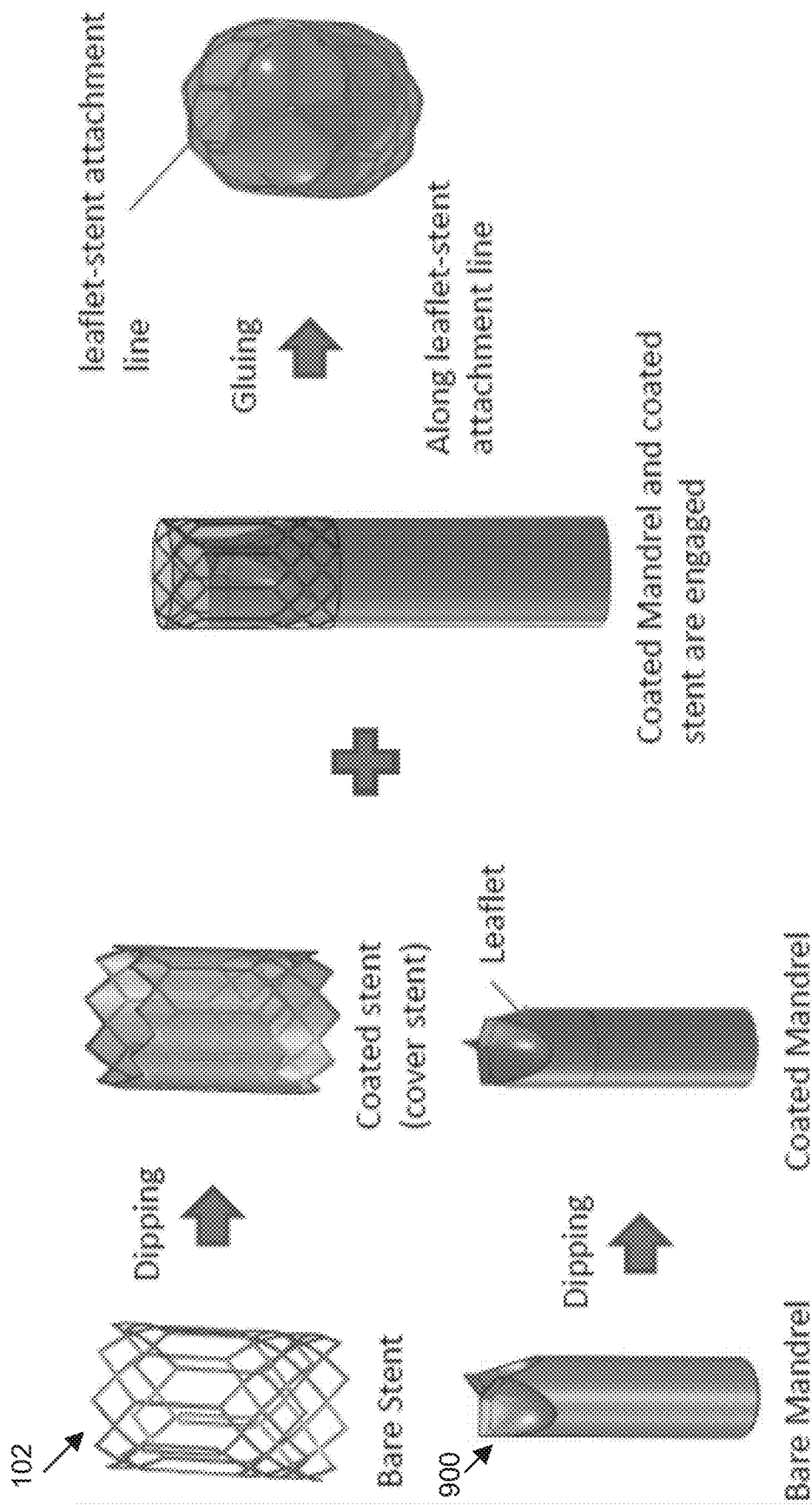
Figure 16:
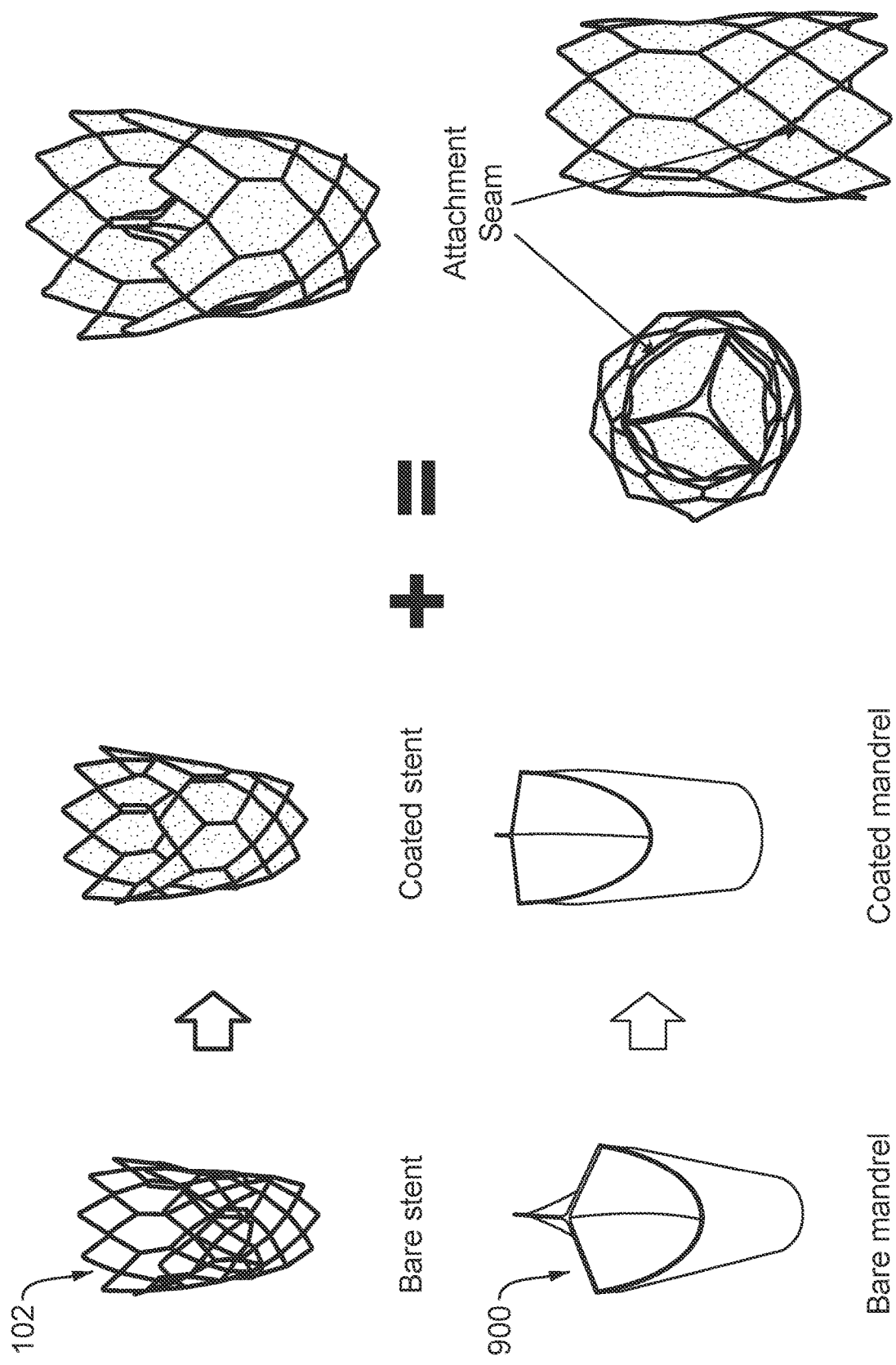
FIG. 16 depict the fabrication of valves according to an embodiment of the invention.

Referring now to FIGS. 15A, 15B, and 16, a method for fabricating a valve is depicted. A bare stent 102 and a bare mandrel 900 are provided.

In some embodiments, the stent 102 can be first coated with a polymer such as PEEK or other metal surface modifier prior to further dip coating of the stent 102 in another polymer in order to improve adhesion of the leaflet polymer 106 to the metal stent 102.

The bare mandrel 900 can optionally be coated with a release agent to promote separation of the polymer leaflets from the mandrel 900.

Both the bare stent 102 and the mandrel 900 are dip coated separately in a polymer, which may be the same or different for the bare stent 102 and the mandrel 900.

The leaflets 106 formed on the mandrel 900 can be removed prior to introduction to the coated stent. Alternatively, the coated mandrel 900 can be introduced into the coated stent, the leaflets 106 can be bonded to the coated stent, and the mandrel 900 can be then be removed to leave the assembled valve 100.

Leaflets 106 can be bonded to the dip-coated stent using a variety of techniques including gluing, chemical fusing (i.e., dissolving the polymers) thermal fusing, sonic welding, stitching, mechanical fastening, and the like. For example, the same polymer solution used to coat either bare stent 102 and/or mandrel 900 can be applied to bond the leaflets 106 to the dip-coated stent.

Although separate fabrication of the polymer-coated stent and the leaflets 106 are currently preferred as a means of avoiding or minimizing air bubbles, the entire valve could be formed in a single dip coating (or series of dip coatings) through use of production-grade manufacturing techniques and other optimizations.

Although dipcoating was successfully used to fabricate prototypes of the valves described herein, any other manufacturing technique capable of producing flexible leaflets can be utilized. Exemplary techniques include injection molding and additive manufacturing or 3D printing.

Referring now to FIGS. 17A and 17B, stent 102 and leaflets 106 can be fabricated based on a diameter that is slightly larger than the placement location as depicted in FIG. 17A. When deployed to a location having a smaller diameter than the manufactured diameter, the leaflets 106 will be held in tight contact with each other as seen in FIG. 17B to form a tight seal. (In order to form a press fit with the vessel wall, the deployed diameter will be greater than the vessel diameter, but less than the manufactured diameter.)

As can be seen in FIGS. 17A and 17B, the coaptation regions of leaflets 106 have a substantially hyperbolic profile both at the manufactured diameter and the deployed diameter.

Figure 17C:
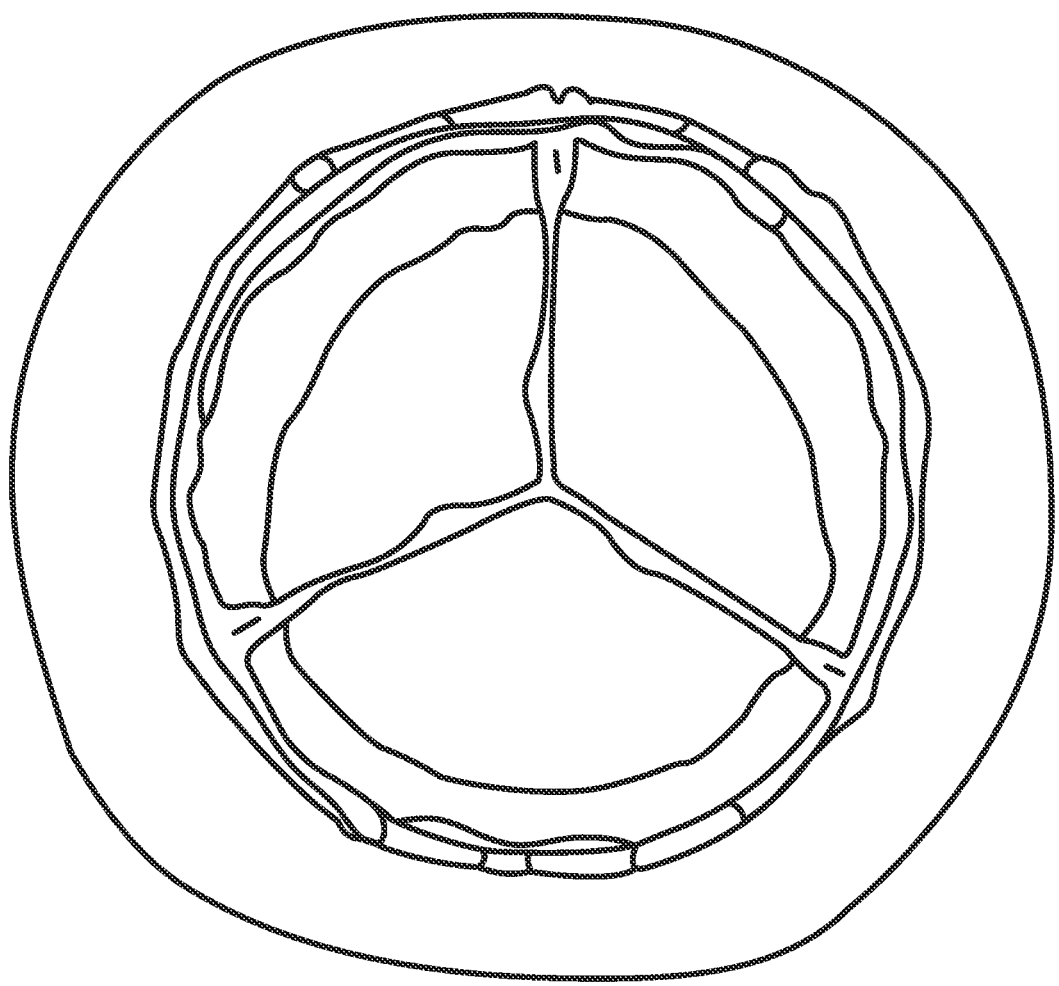
FIG. 17C is a high-speed photograph of a closed valve under pressure according to embodiments of the invention.

Referring now to FIG. 17C, a high-speed photograph of a closed valve under pressure during in vitro testing in a hemodynamic pulse duplicator is provided.

Polymers

The leaflets 106 can be formed from the same or different polymer with which the stent 102 is coated to form wall 104. For example, the leaflets 106 can be formed from polymers such as polyethylene, polyurethane, silicone, and the like. Wall 104 can be formed from polyethylene, polyurethane, silicone, and the like.

Supplementary materials such as directional fibers can mixed into the polymer solution or applied to the leaflets between coatings in order to increase durability The selected polymer can be dissolved by a solvent such as tetrahydrofuran or dimethylacetamide. The thickness of the coated polymer can be controlled as a function of the density of the polymer solution and total number of dippings. When the polymer becomes dry after dipping, the coated stent and mandrel can be placed horizontally and axially rotated in order to produce a constant thickness and prevent the polymer from dripping.

Implantation of Valves

Figure 18:
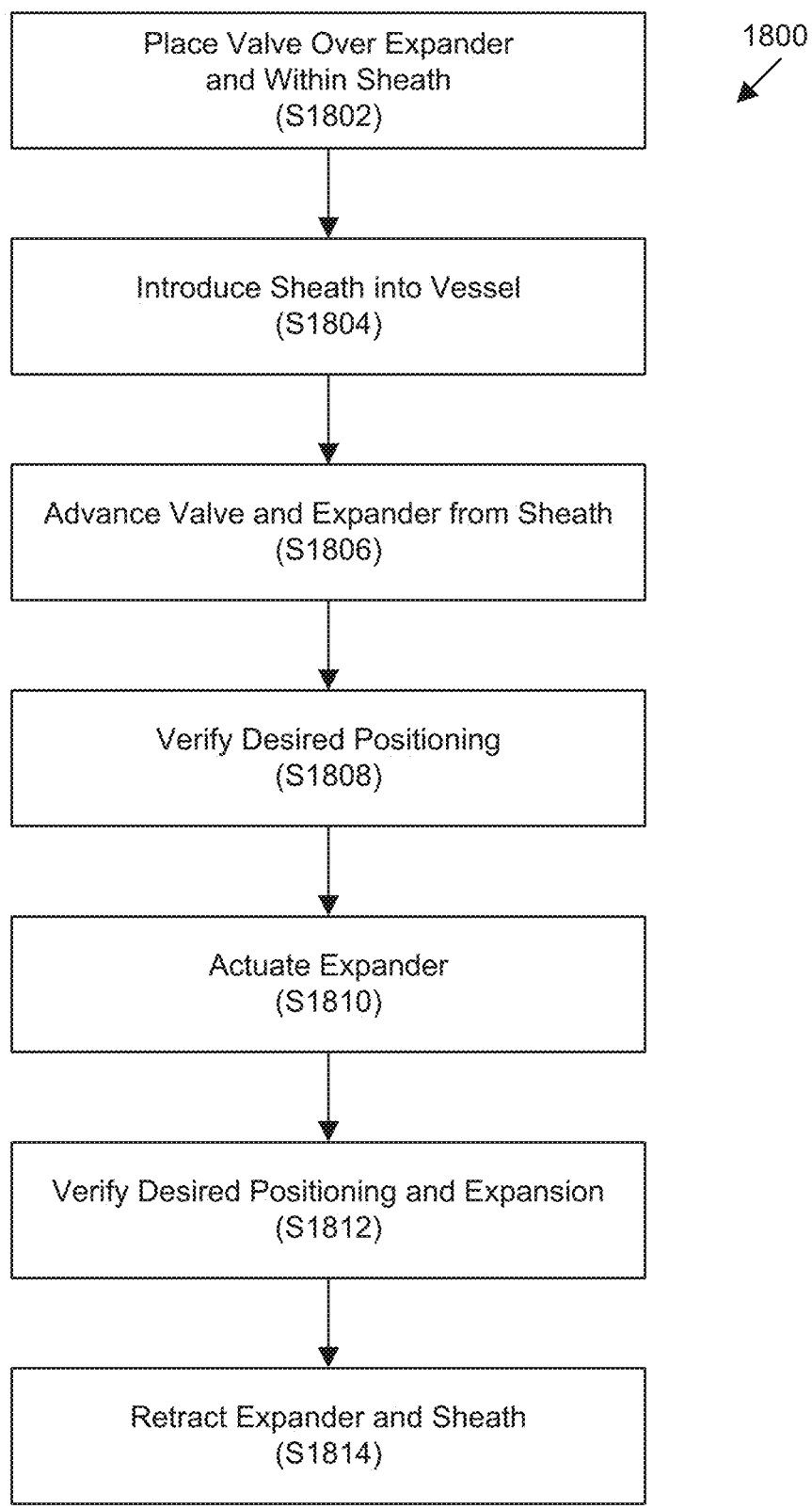
FIG. 18 depicts a method of implanting a valve according to embodiments of the invention.

Referring now to FIG. 18, a method 1800 of implanting an artificial valve is provided. The valve to be implanted can be a valve 100 as described herein.

In step S1802, the valve is placed over an expander and within a sheath. Various surgical expanders and access devices exist in the cardiac surgery field. For example, a balloon catheter could be introduced into a patient's femoral artery and guided to the location of the implanted valve (e.g., within the patient's heart or systemic veins).

In step S1804, the sheath (containing the valve and the expander) is introduced into a vessel of the subject.

In step S1806, the valve and the expander are advanced from the sheath and positioned in the desired location.

In step S1808, the desired positioning can be verified using various imaging techniques such as fiber optics, ultrasound, X-ray, and the like.

In step S1810, the expander is actuated within the valve to expand the valve to form a press fit against the vessel in which the valve is implanted. For example, a balloon catheter can be expanded by introducing gas or a liquid into the balloon.

In step S1812, the desired positioning and expansion can be verified using various imaging techniques such as fiber optics, ultrasound, X-ray, and the like.

In step S1814, the expander and sheath can be retracted according to standard surgical techniques.

Expansion of Implanted Valves

Figure 19:
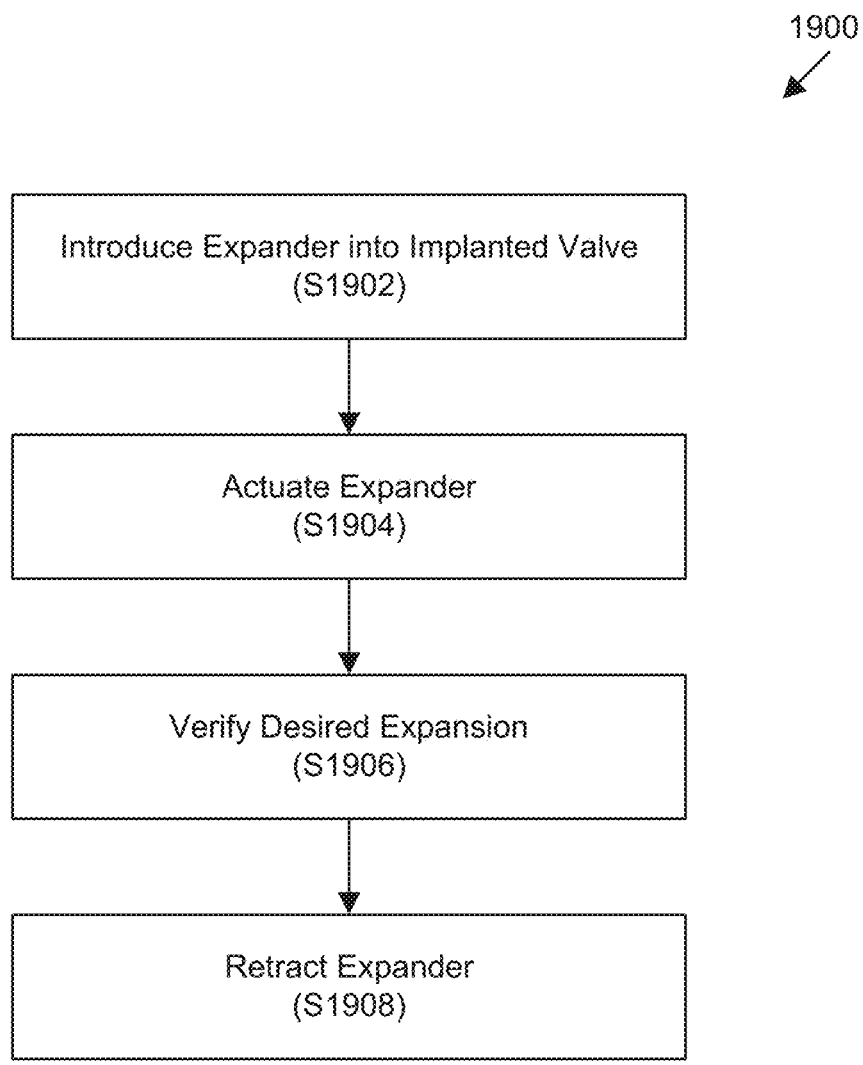
FIG. 19 depicts a method of expanding an implanted valve according to embodiments of the invention.

Referring now to FIG. 19, a method 1900 of expanding an implanted valve is provided. The implanted valve can be a valve 100 as described herein.

In step S1902, an expander is introduced into the implanted valve.

In step S1904, the expander is actuated within the implanted valve to increase the diameter of the implanted valve.

In step S1906, the desired expansion can be verified using various imaging techniques.

In step S1908, the expander can be retracted according to standard surgical techniques.

Surgically-Implanted Valves

Although embodiments of the invention are described and depicted in the context of percutaneous, transcatheter valves having expandable, cylindrical stents, embodiments of the invention described herein can be applied to surgically-implanted valves that generally include anchors having fixed-diameter anchors supporting a plurality of leaflets (e.g., the CARPENTIER-EDWARDS™ series of valves available from Edwards Lifesciences Corporation of Irvine, Calif.). In such embodiments, the anchor replaces the expandable, cylindrical stents described herein.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

What is claimed is:

1. An artificial valve, comprising:
an expandable frame having a compressed, delivery configuration, in which the valve is deliverable to a patient via a catheter, and an expanded, deployed configuration, in which the valve is implantable within the patient, the valve having a first working condition when the frame is in the deployed configuration and expanded to a first diameter and a second working condition when the frame is in the deployed configuration and expanded to a second diameter that is greater than the first diameter; and
a plurality of leaflets disposed within and coupled to the frame, each leaflet from the plurality of leaflets extending from the frame and terminating at a free edge, each free edge having a length that is greater than the first diameter,
the frame has a first open end, a second open end, and a longitudinal axis extending therebetween, the longitudinal axis defining a flow path through the valve,
the frame being formed by a plurality of posts, the plurality of posts including a first set of posts having a first width and a second set of posts having a second width that is greater than the first width,
the first set of posts defining a plurality of cells therebetween that are variable in shape during expansion of the frame, each post from the second set of posts being disposed at a junction between and coupled to two leaflets from the plurality of leaflets, the second set of posts being equal in number to the plurality of leaflets.

2. The artificial valve of claim 1, wherein a first leaflet from the plurality of leaflets is coupled to both a first portion of the frame and a second portion of the frame such that a distance along the free edge of the first leaflet between the first portion of the frame and the second portion of the frame is greater than an arc distance along the frame between the first portion and the second portion when the frame is in the deployed configuration and expanded to the first diameter.

3. The artificial valve of claim 1, wherein:
each leaflet from the plurality of leaflets has a center spaced apart from the leaflet free edge, each free edge of each leaflet having a thickness greater than a thickness of each center of each leaflet from the plurality of leaflets.

4. The artificial valve of claim 1, wherein the frame has a first open end, a second open end, and a longitudinal axis defined therebetween, the longitudinal axis defining a flow path through the valve, the free edge of each leaflet varying along the longitudinal axis of the frame when the frame is in the deployed configuration.

5. The artificial valve of claim 4, wherein the longitudinal axis of the frame is defined between a first open end of the frame and a second open end of the frame, the plurality of leaflets being configured to allow fluid flow from the first open end to the second open end and restrict fluid flow from the second open end to the first open end.

6. The artificial valve of claim 1, wherein the plurality of leaflets are formed of a polymer.

7. The artificial valve of claim 1, wherein each leaflet from the plurality of leaflets is coupled to the frame along a leaflet attachment line, the leaflet attachment line including a curved portion and a linear portion, the curved portion terminating at the linear portion and the linear portion terminating at the free edge of the leaflet, the linear portion being parallel to a longitudinal axis of the frame.

8. The artificial valve of claim 1, wherein each post from the second set of posts defines one or more windows configured to have a fixed shape during expansion of the frame.

9. The artificial valve of claim 8, wherein the second set of posts includes polymer within its one or more windows, each post from the second set of posts being coupled to the two leaflets via the polymer.

10. The artificial valve of claim 8, wherein the one or more windows have a width of about 0.5 mm to about 3 mm, and a height of about 1 mm to about 10 mm, the height being parallel to the longitudinal axis and the width being perpendicular to the longitudinal axis.

11. The artificial valve of claim 8, wherein the one or more windows are rectangular.

12. The artificial valve of claim 8, wherein the one or more windows have a height and a width, the height being greater than the width, the height be parallel to the longitudinal axis and the width being perpendicular to the longitudinal axis.

13. The artificial valve of claim 1, wherein at least a portion of the plurality of cells are covered.

14. The artificial valve of claim 1, wherein at least a portion of the plurality of cells are coated with a polymer.

15. The artificial valve of claim 1, wherein the second set of posts consists of three posts, each of which are circumferentially positioned at 120 degree intervals along the frame, the plurality of leaflets consisting of three leaflets.

16. The artificial valve of claim 1, wherein the plurality of leaflets are coupled to the second set of posts via at least one of a chemical coupling technique, chemical fusing, thermal fusing, or sonic welding.

17. The artificial valve of claim 1, wherein an entire external surface of the frame is covered coated with a polymer.

18. An artificial valve, comprising:
an expandable frame having a compressed, delivery configuration, in which the valve is deliverable to a patient via a catheter, and an expanded, deployed configuration, in which the valve is implantable within the patient; and
a plurality of leaflets disposed within and coupled to the frame, each leaflet from the plurality of leaflets extending from the frame and terminating at a free edge, each free edge having a length that is greater than a diameter of the frame when the frame is in its expanded, deployed configuration,
the frame being formed by a plurality of posts, the plurality of posts including a first set of posts having a first width and a second set of posts having a second width that is greater than the first width, the plurality of posts defining a plurality of cells therebetween,
the plurality of leaflets being coupled to the frame along a leaflet attachment line, the leaflet attachment line traversing one or more posts from the plurality of posts and one or more cells from the plurality of cells.

19. The artificial valve of claim 18, wherein:
the second set of posts includes a post disposed at a junction between and coupled to two leaflets from the plurality of leaflets, the two leaflets defining a commissure region, the post from the second set of posts extending an entire length of the commissure region.

20. The artificial valve of claim 18, wherein:
each post from the second set of posts defines one or more windows configured to have a fixed shape during expansion of the frame.

21. The artificial valve of claim 18, wherein:
each post from the second set of posts defines one or more windows that are covered by a polymer, the plurality of leaflets being coupled to the frame via cohesion to the polymer disposed along the one or more windows and adhesion to the frame.

22. The artificial valve of claim 18, wherein:
one or more cells from the plurality of cells are covered by a polymer, the leaflet attachment line traversing the polymer such that at least a portion of the leaflets are cohesively coupled to the polymer that covers the one or more cells from the plurality of cells.

23. The artificial valve of claim 18, wherein:
each post from the second set of posts defines one or more windows having a width and a height greater than the width, the frame having a first open end, a second open end, and a longitudinal axis extending therebetween and defining a flow path through the valve, the height being parallel to the longitudinal axis and the width being perpendicular to the longitudinal axis.

* * * * *